(12) United States Patent
Holtzman et al.

(10) Patent No.: US 8,444,977 B2
(45) Date of Patent: *May 21, 2013

(54) ASSAY METHOD FOR ALZHEIMER'S DISEASE

(75) Inventors: David M. Holtzman, St. Louis, MO (US); Ronald DeMattos, Noblesville, IN (US); Kelly R. Bales, Coatsville, IN (US); David J. Cummins, Indianapolis, IN (US); Steven M. Paul, Carmel, IN (US)

(73) Assignees: Eli Lilly and Company, Indianapolis, IN (US); Washington University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/834,271

(22) Filed: Jul. 12, 2010

(65) Prior Publication Data

US 2010/0279433 A1 Nov. 4, 2010

Related U.S. Application Data

(63) Continuation of application No. 10/486,908, filed as application No. PCT/US02/26321 on Aug. 16, 2002, now Pat. No. 7,771,722.

(60) Provisional application No. 60/313,221, filed on Aug. 17, 2001, provisional application No. 60/334,987, filed on Oct. 23, 2001, provisional application No. 60/313,224, filed on Aug. 17, 2001.

(51) Int. Cl.
*A61K 39/395* (2006.01)
*A61K 49/00* (2006.01)

(52) U.S. Cl.
USPC ... 424/139.1; 424/9.1; 424/133.1; 424/135.1; 424/152.1

(58) Field of Classification Search
None
See application file for complete search history.

(56) References Cited

U.S. PATENT DOCUMENTS

| | | | |
|---|---|---|---|
| 4,933,156 A | 6/1990 | Quay et al. | |
| 5,004,697 A | 4/1991 | Pardridge | |
| 5,278,049 A | 1/1994 | Baker et al. | |
| 5,593,846 A | 1/1997 | Schenk et al. | |
| 5,688,651 A | 11/1997 | Solomon | |
| 5,693,762 A | 12/1997 | Queen et al. | |
| 5,753,624 A | 5/1998 | McMichael et al. | |
| 5,766,846 A | 6/1998 | Schlossmacher et al. | |
| 5,837,672 A | 11/1998 | Schenk et al. | |
| 5,837,822 A | 11/1998 | Gallatin et al. | |
| 5,851,996 A | 12/1998 | Kline | |
| 5,935,927 A | 8/1999 | Vitek et al. | |
| 6,037,454 A | 3/2000 | Jardieu et al. | |
| 6,114,113 A | 9/2000 | McLaughlin-Taylor et al. | |
| 6,218,506 B1 | 4/2001 | Krafft et al. | |
| 6,582,945 B1 | 6/2003 | Raso | |
| 7,195,761 B2 | 3/2007 | Holtzman et al. | |
| 7,771,722 B2 * | 8/2010 | Holtzman et al. | 424/139.1 |
| 2002/0009445 A1 | 1/2002 | Du et al. | |
| 2002/0058267 A1 | 5/2002 | Ozenberger et al. | |
| 2002/0086847 A1 | 7/2002 | Chain | |
| 2002/0102261 A1 | 8/2002 | Raso | |
| 2004/0265308 A1 | 12/2004 | Schenk | |
| 2005/0019330 A1 | 1/2005 | Schenk | |

FOREIGN PATENT DOCUMENTS

| | | |
|---|---|---|
| EP | 0613007 | 8/1994 |
| EP | 02766022 | 9/2005 |
| WO | WO8901343 | 2/1989 |
| WO | WO9007861 | 7/1990 |
| WO | WO9109967 | 7/1991 |
| WO | WO9618900 | 6/1996 |
| WO | WO9625435 | 8/1996 |
| WO | WO9833815 | 8/1998 |
| WO | WO9844955 | 10/1998 |
| WO | WO9927944 | 6/1999 |
| WO | WO9906066 | 11/1999 |
| WO | WO9960024 | 11/1999 |
| WO | WO0072876 | 12/2000 |
| WO | WO0077178 | 12/2000 |
| WO | WO0110900 | 2/2001 |
| WO | WO0118169 | 3/2001 |
| WO | WO0162801 | 8/2001 |
| WO | WO0162801 A3 | 8/2001 |
| WO | WO0221141 | 3/2002 |
| WO | WO02056237 | 7/2002 |
| WO | WO02060481 | 8/2002 |
| WO | WO03015617 A3 | 1/2004 |
| WO | WO03015617 A2 | 7/2004 |

OTHER PUBLICATIONS

Kotilinek, L.A., et al., "Reversible memory loss in a mouse transgenic model of Alzheimer's disease," J. Neurosci., 22(15):6331-6335 (2002).
Wang, H.-W., et al., "Soluble oligomers of beta amyloid (1-42) inhibit long-term potentiation but not long-term depression in rate dentate gyrus," Brain Research, 924, pp. 133-140 (2002).
Strbak, V., et al., "Passive Immunization and Hypothalamic Peptide Secretion," Neuroendocrinology 1993; 58:210-217.
Ghiso, J., et al., "Epitope map of two polyclonal antibodies that recognize amyloid lesions in patients with Alzheimer's disease," Biochem J., 282 (Pt. 2), pp. 517-522 (1992).
Ragusi, C., et al., "Redistribution of Imipramine from Regions of the Brain Under the Influence of Circulating Specific Antibodies," J. Neurochem., vol. 70, No. 5, pp. 2099-2105 (1998).

(Continued)

*Primary Examiner* — Elizabeth C Kemmerer
*Assistant Examiner* — Kimberly A Ballard
(74) *Attorney, Agent, or Firm* — McAndrews, Held & Malloy, Ltd.

(57) ABSTRACT

A diagnostic test for preclinical and clinical Alzheimer's disease is based on plasma levels of $A\beta_{40}$, $A\beta_{42}$, their ratio, or their rate of entry following administration of antibodies that sequester $A\beta$. Alterations of any of these parameters from control values identifies preclinical or clinical Alzheimer's disease.

12 Claims, 6 Drawing Sheets

OTHER PUBLICATIONS

Suo, Z., et al., "Soluble Alzheimers beta-amyloid constricts the cerebral vasculature in vivo," Neuroscience Letters, 257, pp. 77-80 (1998).

Lue, L., et al., "Soluble Beta-amyloid Peptide Concentration as a Predictor of Synaptic Change in Alzheimer's Disease,", Am. J. Pathol., 1999, 155: pp. 853-862.

Esler, W., et al., "Point substitution in the central hydrophobic cluster of a human beta-amyloid congener disrupts peptide folding and abolishes plaque competence," Biochemistry, vol. 35, pp. 13914-13921 (1996).

Maggio, J. & Mantyh, P., "Brain Amyloid—A Physicochemical Perspective," Brain Pathology, vol. 6, 147-162 (1996).

Gorevic, P., et al., "Ten to fourteen residue peptides of Alzheimer's disease protein are sufficient for amyloid fibril formation and its characteristic X ray diffraction pattern," Biochem. and Biophy. Res. Commun., vol. 147, No. 2 (1987).

Balbach, J., et al., "Amyloid fibril formation by Abeta 16-22, a seven-residue fragment of the Alzheimer's beta-amyloid peptide, and structutal characterization by solid state NMR," Biochemistry, vol. 39, pp. 13748-13759 (2000).

Simmons, L., "Secondary structure of amyloid beta peptide correlates with neurotoxic activity In Vitro," Molecular Pharmacology, vol. 45, pp. 373-379 (1994).

Wood, A., et al., "Prolines and amyloidogenicity in fragments of the Alzheimer's peptide Beta/A4," Biochemistry, vol. 34, pp. 724-730 (1995).

Xu, S. and Gaskin, F., "Increased incidence of anti-beta-amyloid autoantibodies secreted by Epstein-Barr virus transformed B cell lines from patients with Alzheimer's disease," Mechanisms of Ageing and Development, vol. 94, pp. 213-222 (1997).

Soto, C., et al., "The alpha-helical to beta-strand transition in the amino-terminal fragment of the amyloid beta-peptide modulates amyloid formation," J. Biol. Biol. Chem., vol. 270, No. 7, pp. 3063-3067 (1995).

Tjernberg, L., et al., "A molecular model for Alzheimer amyloid beta-peptide fibril formation," J. Biol. Biol. Chem., vol. 274, No. 18, pp. 12619-12625 (1999).

Hilbich, C., et al., "Substitutions of hydrophobic amino acid reduce the amyloidogenicity of Alzheimer's disease BetaA4 peptides," J. Mol. Biol., vol. 228, pp. 460-473 (1992).

Hilbich, C., et al., "Human and rodent sequence analogs of Alzheimer's amyloid BetaA4 share similar properties and can be solubized in buffers of pH 7.4," Eur. J. Biochem., vol. 201, pp. 61-69 (1991).

Hilbich, C., et al., "Aggregation and secondary structure of synthetic amyloid BetaA4 peptides of Alzheimer's disease," J. Mol. Biol., vol. 218, pp. 149-163 (1991).

Pillot, T., et al., "Fusogenic Properties of the C-terminal Domain of the Alzheimer Beta-Amyloid Peptide," J. Biol. Chem., vol. 271, No. 24, pp. 28757-28765 (1996).

Hartman, R.E., et al., "Treatment with an Amyloid-B Antibody Amerliorates Plaque Load, Learning Deficits, and Hippocampal Long-Term Potentiation in a Mouse Model of Alzheimer's Disease," J. Neuroscience, vol. 25, No. 26, pp. 6213-6220 (2005).

Shefner, et al., "A Novel Class of Anti-DNA Antibodies Identified in BALB/c Mice", J. Exp. Med., 173:287-296 (1991).

Raaphorst, et al., "Restricted utilization of germ-line VH3 genes and short diverse third complementarity-determining regions (CDR3) in human fetal B lymphocyte immunoglobulin heavy chain rearrangements", Eur. J. Immunol, 22, 247-251 (1992).

BIAcore history from www.biacore.com/lifesciences/history/index.html, Jul. 15, 2008.

Darling et al., "Glycosylation of Erythropoietin Affects Receptor Binding Kinetics: Role of Electrostatic Interactions", Biochemistry, 41:14524-14531 (2002).

Harris et al., "Profiles for the analysis of immunoglobulin sequences: Comparison of V gene subgroups", Protein Science, 4:306-310 (1995).

Katsamba et al., "Kinetic analysis of a high-affinity antibody/antigen interaction performed by multiple Biacore users", Anal. Bichem. 352 208-211 (2006).

Landolfi et al., "The Integrity of the Ball-and-Socket Joint Between V and C Domains Is Essential for Complete Activity of a Humanized Antibody", The Journal of Immunology, 166:1748-1754 (2001).

Mehta et al., "Plasma and Cerebrospinal Fluid Levels of Amyloid β Proteins 1-40 and 1-42 in Alzheimer Disease", Arch Neurol. 57(1):100-105 (2000).

Myszka et al., "Equilibrium Analysis of High Affinity Interactions Using BIACORE1" Analytical Biochemistry, 265:326-330 (1998).

Nieba et al., "Competition BIAcore for Measuring True Affinities: Large Differences from Values Determined from Binding Kinetics", Analytical Biochemistry, 234:155-165 (1996).

Padlan, "A Possible Procedure for Reducing the Immunogenicity of Antibody Variable Domains While Preserving Their Ligand-Binding Properties", Molecular Immunology, 28(4/5):489-498 (1991).

Skoog, "Detection of Preclinical Alzheimer's Disease", N Eng J Med, Aug. 2000; 343:502-503.

Tsurushita et al., "Design of humanized antibodies: From anti-Tac to Zenapax", Methods, 36:69-83.

Seubert, P. et al., "Isolation and quantification of soluble Alzheimer's beta-peptide from biological fluids", Nature, 359, pp. 325-327 (1992).

Gaskin F. et al., "Human antibodies reactive with beta-amyloid protein in Alzheimer's disease", Journal of Experimental Medicine, 177 (4) 1181-1186 (1993).

Solomon B. et al., "Disaggregation of Alzheimer beta-amyloid by site-directed mAb", Proc. Natl. Acad. Sci. USA 94(8), pp. 4109-4112 (1997).

Blass J.P. "Immunologic Treatment of Alzheimer's Disease", NEJM, 341, pp. 1694-1695 (1999).

Kuo Y.M. et al., "High levels of circulating Abeta42 are sequestered by plasma proteins in Alzheimer's disease", Biochem Biophys Res Commun, 257(3), pp. 787-791 (1999).

Janus C., et al., "AB peptide immunization reduces behavioural impairment and plaques in a model of Alzheimer's disease", Nature, vol. 408, pp. 979-982 (2000).

Zlokovic B.V. et al., "Clearance of amyloid B-peptide from brain: transport or metabolism?", Nature Mediine, vol. 6(7), pp. 718-719 (2000).

DeMattos R.B. et al., "Peripheral anti-Abeta antibody alters CNS and plasma Abeta clearance and decreases brain Ab burden in a mouse model of Alzheimer's disease", PNAS, vol. 98(15), pp. 8850-8855 (2001).

Lee VM-Y. et al., "AB immunization: Moving AB peptide from brain to blood", PNAS, vol. 98(16), pp. 8931-8932 (2001).

Town T. et al., "Characterization of murine immunoglobulin G antibodies against human amyloid-B1-42", Neuroscience Letters, vol. 307, pp. 101-104 (2001).

DeMattos R.B. et al., "Plaque-associated disruption of CSF and plasma amyloid-B (AB) equilibrium in a mouse model of Alzheimer's disease", J Neurochem, 81:229-236 (2002).

DeMattos R.B. et al., "Brain to Plasma Amyloid-B Efflux: a Measure of Brain Amyloid Burden in a Mouse Model of Alzheimer's Disease", Science, Mar. 22, 2002, vol. 295, pp. 2264-2267.

Bard Frederique et al., Peripherally administered antibodies against amyloid B-peptide enter the central nervous system and reduce pathology in a mouse model of Alzheimer disease, Nature Medicine, vol. 6, No. 8, Aug. 2000, pp. 916-919.

Growdon JH, Biomarkers of Alzheimer Disease, Arch Neurol. Mar. 1999, 56(3): 281-283.

Webster's New World Dictionary, Third College Edn., Webster's New World, New York, 1988, entry for "preclinical", p. 1061.

Lippa CF et al., Aberta-42 deposition precedes other changes in PS-1 Alzheimer's disease, Lancet, Oct. 3, 1998, vol. 352, No. 9134, pp. 1117-1118.

Matsuda, et al., J. Exp. Med., 188(11):2151-2162 (1998).

Lautner-Rieske, et al ., Eur. J. Immunol., 22:1023-1029 (1992).

Tomlinson, et al., J. Mol. Biol., 227:776-798 (1992).

Cox, et al., Eur. J. Immunol, 24:827-836 (1994).

Schable, et al., Eur J. Immunol., 29:2082-2086 (1999).

Langdon, et al., Immunogenetics, 51:241-245 (2000).

Ollo, et al., Nucleic Acids Research, 11(22):7877-97 (1983).

Riechmann, et al., Nature, 332:323-27 (1988).

Co, et al ., Proc. Natl. Acad. Sci., 88:2869-73 (1991).

Carter, et al., Proc. Natl. Acad. Sci., 89:4285-89 (1992).
Hieter, et al., Cell, 22:197-207 (1980).
Hieter, et al., J. Biol. Chem., 257(3):1516-22 (1982).
Levitt M., "Molecular dynamics of native protein," J. Mol. Biol., 168:595-620 (1983).
Queen, C., et al., "A humanized antibody that binds to the interleukin 2 receptor," Proc. Natl. Acad. Sci. USA, 86 10029-10033 (1989).
Burdick, D., et al., "Assembly and Aggregation Properties of Synthetic Alzheimer's A4/Beta Amyloid Peptide Analogs", Journal of Biological Chemistry, vol. 267, pp. 546-555 (1992).
Co, M.S., et al., "Chimeric and humanized antibodies with specificity for the CD33 antigen," J. Immunol., 148:1149-1154 (1992).
Haass, C., et al., "Amyloid beta-peptide is produced by cultured cells during normal metabolism," Nature, 359, pp. 322-325 (1992).
Flood, J. F., et al., "An amyloid beta-protein fragment, A Beta [12-28], equipotently impairs post-training memory processing when injected into different limbic system structures," Brain Research, vol. 663(2), pp. 271-276 (1994).
Koudinov, A., et al., "The soluble form of Alzheimer's amyloid beta protein is complexed to high density lipoprotein 3 and very high density lipoprotein in normal human plasma," Biochem. & Biophysical Research Communications, vol. 205, pp. 1116-1171 (1994).
Schwarzman AL, et al., "Transthyretin sequesters amyloid beta protein and prevents amyloid formation," Proc. Natl. Acad. Sci., vol. 91, pp. 8368-8372 (1994).
Tabaton M., et al., "Soluble Amyloid Beta-Protein is a Marker of Alzheimer Amyloid in Brain But Not in Cerebrospinal Fluid," Biochemical and Biophysical Research Communications, vol. 200(2), pp. 1598-1603 (1994).
Walker, L.C., et al., "Labeling of cerebral amyloid in vivo with a monoclonal antibody," J. Neuropathol Exp. Neurol., vol. 53(4), pp. 377-383 (1994).
Wisniewski, T., et al., "Alzheimer's disease and soluble A beta," Neurobiol. Aging, 15(2), pp. 143-152, Review (1994).
Giulian, D., et al., "Specific Domains of Beta-Amyloid from Alzheimer Plaque Elicit Neuron Killing in Human Microglia," J. Neuroscience, vol. 16(19), pp. 6021-6037 (1996).
Hanan, E., et al., "Inhibitory effect of monoclonal antibodies on Alzheimer's beta amyloid peptide aggregation," Int. J. Exp. Clin. Invest., 3, pp. 130-133 (1996).
Solomon, B., et al., "Monoclonal antibodies inhibit in vitro fibrillar aggregation of the Alzheimer beta-amyloid peptide," Proc. Natl. Acad. Sci. USA, vol. 93(1), pp. 452-455 (1996).
Teller, J.K., et al., "Presence of soluble amyloid beta-peptide precedes amyloid plaque formation in Down's syndrome," Nature Medicine, vol. 2(1), pp. 93-95 (1996).
Tjernberg, L.O., et al., "Arrest of beta-amyloid fibril formation by a pentapeptide ligand," J. Biol. Chem. 271(15), pp. 8545-8548 (1996).
Winter, G., et al., "Humanized Antibodies," Immunology Today, 14(6), 243-246 (1993).
El-Agnaf, O.M., et al, "The influence of the central region containing residues 19-25 on the aggregation properties and secondary structure of Alzheimer's beta-amyloid peptide," Eur. J. Biochem. 256(3), pp. 560-569 (1998).
He X-Y, et al., Humanization and pharmacokinetics of a monoclonal antibody for both E- and P-selectin, J. Immunol., 160:1029-1035 (1998).
Lambert, M.P., et al., "Diffusible, nonfibrillar ligands derived from Abeta1-42 are potent central nervous system neurotoxins," Proc. Natl. Acad. Sci., 95:6448-6453 (1998).
Solomon, B., et al., "The Amino Terminus of the Beta-Amyloid Peptide Contains an Essential Epitope for Maintaining its Solubility," Progress in Alzheimer's and Parkinson's Diseases, pp. 205-211 (1998).
Soto, C., et al., Beta-sheet breaker peptides inhibit fibrillogenesis in a rat brain model of amyloidosis: Implications of Alzheimer's therapy, Nature Medicine, vol. 4(7), pp. 822-826 (1998).
McLean, C., et al., "Soluble Pool of Abeta Amyloid as a Determinant of Severity of Neurodegeneration in Alzheimer's Disease," Amer. Neurological Assoc., vol. 46, pp. 860-866 (1999).
Schenk, D., et al., "Immunization with amyloid-beta attenuates Alzheimer-disease-like pathology in the PDAPP mouse," Nature, vol. 400, pp. 173-177 (1999).
St. George-Hyslop, P., et al., "Antibody clears senile plaques," Nature, vol. 400, pp. 116-117 (1999).
Wang, J., et al., "The Levels of Soluble versus Insoluble Brain Abeta Distinguish Alzheimer's Disease from Normal and Pathologic Aging," Experimental Neurology, vol. 158, pp. 328-377 (1999).
Games, D., et al., "Prevention and Reduction of AD-type Pathology in PDAPP Mice Immunized with Abeta1-42," Annals of N.Y. Acad. Sci., vol. 920, pp. 274-284 (2000).
Levy, A., et al., "Immunization for Alzheimer's Disease: A shot in the Arm or a Whiff?," American Neurological Assoc., vol. 48, pp. 553-554 (2000).
Morgan, D., et al., "Abeta peptide vaccination prevents memory loss in an animal model of Alzheimer's disease," Nature, vol. 408, pp. 982-985 (2000).
Naslund, J., et al., "Correlation Between Elevated Levels of Amyloid Beta Peptide in the Brain and Cognitive Decline," J. Am. Med. Assoc., 283:1571 (2000).
Arendash, G.W., et al., "Behavioral Assessment of Alzheimer's Transgenic Mice Following Long-Term Abeta Vaccination: Task Specificity and Correlations between Abeta Deposition and Spatial Memory," DNA and Cell Biology, vol. 20(11), pp. 737-744 (2001).
Bacskai, B.J., et al., "Imaging of amyloid-beta deposits in brains of living mice permits direct observation of clearance of plaques with immunotherapy," Nature Medicine, vol. 7(3), pp. 369-372 (2001).
Dickey, C.A., et al., "Duration and Specificity of Humoral Immune Responses in Mice Vaccinated with the Alzheimer's Disease-Associated Beta-Amyloid 1-42 peptide," DNA and Cell Biology, vol. 20(11), pp. 723-729 (2001).
Esiri, M.M., et al, "Is an effective immune intervention for Alzheimer's disease in prospect?," Trends Pharmacol. Sci. 22(1), pp. 2-3 (2001).
Haass, C., et al., "Protofibrils, the unifying toxic molecule of neurodegenerative disorders?," Nature Neuroscience, vol. 4(9), pp. 859-860 (2001).
Klein, W.L., et al., "Targeting small Abeta oligomers: the solution to an Alzheimer's disease conundrum?," Trends in Neurosciences, vol. 24(4), pp. 219-224 (2001).
Lambert, M.P., et al., "Vaccination with soluble Abeta oligomers generates toxicity-neutralizing antibodies," Journal of Neurochemistry, vol. 79, pp. 595-605 (2001).
Poduslo, J.F., et al., "Permeability of proteins at the blood-brain barrier in the normal adult mouse and double transgenic mouse model of Alzheimer's disease," Neurobiol. Dis., 8(4):555-67 (2001).
Feb. 21, 2006 Non-Final Office Action in U.S. Appl. No. 10/486,908.
Aug. 29, 2007 Non-Final Office Action in U.S. Appl. No. 10/486,908.
Jul. 15, 2008 Non-Final Office Action in U.S. Appl. No. 10/486,908.
Jan. 16, 2009 Final Office Action in U.S. Appl. No. 10/486,908.
Mar. 24, 2009 Final Office Action in U.S. Appl. No. 10/486,908.
Aug. 27, 2009 Non-Final Office Action in U.S. Appl. No. 10/486,908.
Mar. 10, 2010 Notice of Allowance in U.S. Appl. No. 10/486,908.
Tsurushita et al., "Design of humanized antibodies: From anti-Tac to Zenapax", Methods, 36:69-83, (2005).

* cited by examiner

A

B

C

| Plasma Aβ Correlation's with Alzheimer-Like Pathology in Hippocampus | | | | | | | | |
|---|---|---|---|---|---|---|---|---|
| Plasma Aβ correlation with Aβ load and fibrillar amyloid | | | | | | | | |
| | | Pre-Bleed | 5-Min | 1-Hour | 3-Hour | 6-Hour | 24-Hour | AUC |
| Plasma Aβ40: | | | | | | | | |
| Aβ Load: | Pearson r | -0.0158 | 0.5527 | 0.5904 | 0.4310 | 0.5533 | 0.5932 | 0.7056 |
| | P value | 0.9209 | <0.0001 | <0.0001 | 0.0014 | <0.0001 | <0.0001 | <0.0001 |
| Amyloid Load: | Pearson r | 0.1535 | 0.7420 | 0.6257 | 0.7053 | 0.6684 | 0.7432 | 0.7624 |
| | P value | 0.3378 | <0.0001 | <0.0001 | <0.0001 | <0.0001 | <0.0001 | <0.0001 |
| Plasma Aβ42: | | | | | | | | |
| Aβ Load: | Pearson r | -0.0614 | 0.2223 | -0.0036 | 0.1309 | 0.4551 | 0.3391 | 0.5322 |
| | P value | 0.6817 | 0.1207 | 0.9798 | 0.3549 | 0.0008 | 0.0139 | <0.0001 |
| Amyloid Load: | Pearson r | 0.0443 | 0.4790 | 0.2321 | 0.3996 | 0.4476 | 0.6062 | 0.6214 |
| | P value | 0.7698 | 0.0005 | 0.1013 | 0.0037 | 0.0011 | <0.0001 | <0.0001 |
| Aβ40/42 Ratio: | | | | | | | | |
| Aβ Load: | Pearson r | 0.0369 | 0.5223 | 0.6888 | 0.4215 | 0.1754 | 0.7190 | 0.6138 |
| | P value | 0.8236 | <0.0001 | <0.0001 | 0.0019 | 0.2183 | <0.0001 | <0.0001 |
| Amyloid Load: | Pearson r | 0.1293 | 0.4825 | 0.5047 | 0.4364 | 0.2843 | 0.6029 | 0.5510 |
| | P value | 0.4393 | 0.0004 | 0.0002 | 0.0014 | 0.0454 | <0.0001 | <0.0001 |

Figure 6

ASSAY METHOD FOR ALZHEIMER'S DISEASE

CROSS REFERENCE TO RELATED APPLICATIONS

This application is a continuation of U.S. application Ser. No. 10/486,908, filed Feb. 17, 2004 now U.S. Pat. No. 7,771,722, which was filed as a national stage entry of International Application Number PCT/US02/26321, which was filed on Aug. 16, 2002, and claims the benefit of U.S. Application Ser. No. 60/313,221, which was filed on Aug. 17, 2001, and U.S. Application Ser. No. 60/334,987, which was filed on Oct. 23, 2001, the contents of which are incorporated herein by reference in their entireties. This application is also related to U.S. Application Ser. No. 60/313,224, which was filed on Aug. 17, 2001, the contents of which are incorporated herein by reference in its entirety.

TECHNICAL FIELD

The invention relates to an assay which permits diagnosis of preclinical and clinical Alzheimer's disease. The test relies on assessing the levels of amyloid beta (A$\beta$) peptide in plasma following administration of certain anti-A$\beta$ antibodies to a subject.

BACKGROUND ART

A number of symptomologies which result in cognitive deficits, stroke, brain hemorrhage, and general mental debilitation appear to be associated with neuritic and cerebrovascular plaques in the brain containing the amyloid beta peptide (A$\beta$). Among these conditions are both preclinical and clinical Alzheimer's disease, Down's syndrome, and preclinical and clinical cerebral amyloid angiopathy (CAA). The amyloid plaques are formed from amyloid beta peptides. These peptides circulate in the blood and in the cerebrospinal fluid (CSF). The A$\beta$ peptide in circulating form is composed of 39-43 amino acids (mostly 40 or 42 amino acids) resulting from the cleavage of a common precursor protein, amyloid precursor protein, often designated APP.

Evidence suggests that A$\beta$ can be transported back and forth between brain and the blood (Ghersi-Egea, J-F., et al. *J. Neurochem.* (1996) 67:880-883; Zlokovic, B. V., et al., *Biochem. Biophys. Res. Comm.* (1993) 67:1034-1040; Shibata, M., et al., *J. Clin. Invest.* (2000)106:1489-1499. Further A$\beta$ in plaques is in an equilibrium with soluble A$\beta$ in the brain and blood (Kawarabayashi, T., et al., *J. Neurosci.* (2001) 21:372-381), DeMattos et al., *Proc. Natl. Acad. Sci USA* (2001) 98:8850-8855.

As described in PCT application US00/35681 and U.S. Ser. No. 09/153,130 both incorporated herein by reference, total circulating levels of A$\beta$ peptide in CSF are similar in normal individuals and individuals predisposed to exhibit the symptoms of Alzheimer's. However, A$\beta_{42}$ levels are lower on average in individuals with Alzheimer's disease (Nitsch, R. M., et al., *Ann. Neurol.* (1995) 37:512-518). It is known that A$\beta_{42}$ is more prone to aggregate than is A$\beta_{42}$, and when this happens, adverse consequences such as A$\beta$ deposition in amyloid plaques, conversion of A$\beta$ to toxic forms, nerve cell damage, and behavioral impairment such as dementia ensue (Golde, T. E., et al., *Biochem. Biophys. Acta.* (2000) 1502:172-187).

PCT application PCT/US01/06191 entitled "Humanized Antibodies That Sequester A$\beta$ Peptide" filed 26 Feb. 2001 and incorporated herein by reference describes antibodies which do not appreciably cross the blood-brain barrier and which sequester A$\beta$ peptides circulating in biological fluids. These antibodies are described as useful for preventive and therapeutic treatment of conditions associated with the formation of A$\beta$-containing diffuse, neuritic, and cerebrovascular plaques in the brain. The application describes administering the antibodies and then measuring circulating levels of A$\beta$ peptide in blood in order to assess the progress of therapy. There is no clear suggestion, however, that the levels of A$\beta$ peptide following administration of the antibodies are diagnostic of the condition itself. The present invention resides in the surprising result that enhanced levels of both A$\beta_{40}$ and A$\beta_{42}$ as well as the A$\beta_{40}$/A$\beta_{42}$ ratio correlate with the levels of A$\beta$ peptide deposition in the brain when the antibodies are administered to an individual. Thus, measurement of these components in the blood after administration of the antibody provides a simple straightforward diagnostic test for both clinical and preclinical Alzheimer's disease and related neurological disorders.

There are additional relevant publications concerning the behavior of A$\beta$ peptide antibodies. For example, PCT publication WO99/27944 published 10 Jun. 1999 describes methods to induce an immune response in order to reduce amyloid deposits. Publication No. WO99/60024 published 25 Nov. 1999, describes methods for amyloid removal using anti-amyloid antibodies. Additional PCT publications, including WO00/72880, WO00/72876 and WO00/77178 all describe various activities of anti-A$\beta$ peptide antibodies. Antibodies directed to the N-terminus of this peptide are said to reduce plaques in a transgenic murine model; immunization with the amyloid itself is described as are antibodies designed to catalyze hydrolysis of the peptide.

It has been shown that one pathway for A$\beta$ metabolism is via transport from CNS to the plasma (Zlokovic, B. V., et al., *Proc. Natl. Acad. Sci (USA)* (1996) 93:4229-4234; Ghersi-Egea, J-F., et al., *J. Neurochem.* (1996)67:880-883). Additionally, it has been shown that A$\beta$ in plasma can cross the blood-brain-barrier and enter the brain (Zlokovic, B. V., et al., *Biochem. Biophys. Res. Comm.* (1993) 67:1034-1040). It has also been shown that administration of certain polyclonal and monoclonal A$\beta$ antibodies decreases A$\beta$ deposition in amyloid plaques in the App$^{V717F}$ transgenic mouse model of Alzheimer's disease (Bard, F., et al., *Nature Med.* (2000) 6:916-919). This was said to be due to certain anti-A$\beta$ antibodies crossing the blood-brain-barrier and stimulating phagocytosis of amyloid plaques by microglial cells. In Bard's experiments, assays of brain slices ex vivo showed that the presence of added A$\beta$ antibody, along with exogenously added microglia, induced phagocytosis of A$\beta$, resulting in removal of A$\beta$ deposits.

The levels of both soluble A$\beta_{40}$ and A$\beta_{42}$ in CSF and blood can readily be detected using standardized assays using antibodies directed against epitopes along the A$\beta$ chain. Such assays have been reported, for example, in U.S. Pat. Nos. 5,766,846; 5,837,672; and 5,593,846. These patents describe the production of murine monoclonal antibodies to the central domain of the A$\beta$ peptide, and these were reported to have epitopes around and including positions 16 and 17. Antibodies directed against the N-terminal region were described as well. Several monoclonal antibodies were asserted to immunoreact with positions 13-28 of the A$\beta$ peptide; these did not bind to a peptide representing positions 17-28, thus, according to the cited patents, establishing that it is this region, including positions 16-17 (the $\Diamond$-secretase site) that was the target of these antibodies. Among antibodies known to bind between amino acids 13 and 28 of A$\beta$ are mouse antibodies 266 (m266), 4G8, and 1C2.

DISCLOSURE OF THE INVENTION

It has now been found that antibodies which are useful for performing assays for Aβ peptide, and which are useful in treatment of conditions associated with amyloid plaques in the brain can elicit a response which results in a marked increase in the level of Aβ peptide in the blood and this level can be used as a diagnostic marker for clinical and preclinical Alzheimer's disease. These antibodies, which may or may not be humanized, sequester Aβ peptide from its bound, circulating form in blood and alter clearance of soluble and bound forms of Aβ in central nervous system and plasma. These antibodies, and fragments thereof, specifically bind to an epitope between amino acids 13 and 28 of the Aβ molecule. The CDR of these antibodies can be derived from mouse monoclonal antibody 266 (SEQ ID NO:1 through SEQ ID NO:6). Useful antibodies include antibodies and fragments thereof, wherein the variable regions have sequences comprising the CDR from mouse antibody 266 and specific human framework sequences (SEQ ID NO:7 through SEQ ID NO:10), wherein the antibodies retain approximately the binding properties of the mouse antibody and have in vitro and in vivo properties functionally equivalent to the mouse antibody 266. Especially useful are humanized antibodies and fragments thereof, wherein the light chain is SEQ ID NO:11 and the heavy chain is SEQ ID NO:12.

Thus, in one aspect, the invention is directed to a method to diagnose Alzheimer's disease in a subject at both a clinical and preclinical stage which method comprises administering to said subject an amount of an antibody that sequesters Aβ peptide from its bound, circulating form in blood, and alters clearance of soluble and bound forms of Aβ in the central nervous system in plasma, or which specifically binds an epitope contained within positions 13-28 of Aβ, preferably an antibody having an immunoreactivity equivalent to mouse antibody 266 effective to alter the levels of circulating Aβ peptides in the blood of said subject when said subject is in a clinical or preclinical stage of Alzheimer's disease followed by measuring the level of $A\beta_{40}$, $A\beta_{42}$, or the ratio of $A\beta_{40}/A\beta_{42}$ in the blood of said subject, wherein an enhanced concentration of $A\beta_{40}$, $A\beta_{42}$ and/or $A\beta_{40}/A\beta_{42}$ ratio in said subject identifies said subject as in a preclinical or clinical stage of Alzheimer's disease or cerebral amyloid angiopathy. In other aspects, the invention is directed to kits containing the appropriate materials for conducting the diagnostic method.

BRIEF DESCRIPTION OF THE DRAWINGS

FIG. 6 is a table showing Pearson correlation coefficients (Pearson r) and significance (P value) determined between plasma Aβ values (pre and post injection of m266) and hippocampal Aβ or amyloid load.

MODES OF CARRYING OUT THE INVENTION

Figure 1:
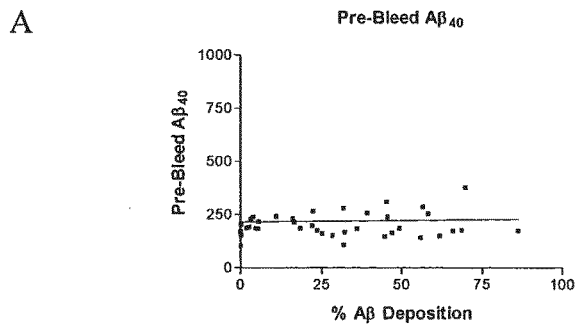
FIGS. 1A, B and C are graphs showing the levels of $A\beta_{40}$ (FIG. 1A), $A\beta_{42}$ (FIG. 1B), and $A\beta_{40}/A\beta_{42}$ ratio (FIG. 1C) in plasma of transgenic mice prior to administration of the antibody m266, and the lack of correlation with brain Aβ deposits.
Figure 1:
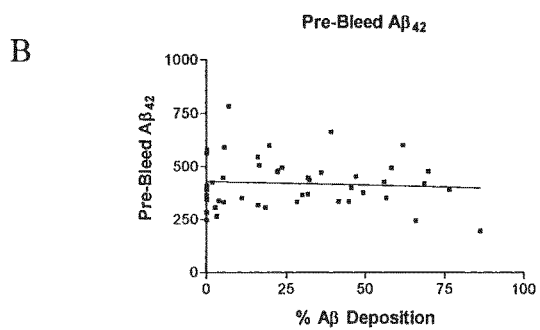
Figure 1:
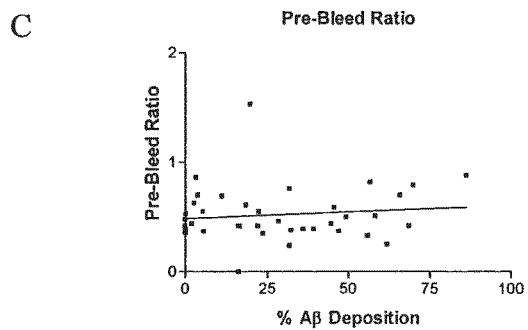

The Aβ peptides that circulate in human biological fluids represent a carboxy terminal region of a precursor protein encoded on chromosome 21. It has been reported from the results of in vitro experiments that the Aβ peptide has poor solubility in physiological solutions, since it contains a stretch of hydrophobic amino acids which are a part of the region that anchors its longer precursor to the lipid membranes of cells. It is thus not surprising that circulating Aβ peptide is normally complexed with other moieties that prevent it from aggregating. This has resulted in difficulties in detecting circulating Aβ peptide in biological fluids.

The above-mentioned patent documents (U.S. Pat. Nos. 5,766,846; 5,837,672 and 5,593,846) describe the preparation of antibodies, including a monoclonal antibody, designated clone 266 (m266), which was raised against, and has been shown to bind specifically to, a peptide comprising amino acids 13-28 of the Aβ peptide. Applicants have found that after administering m266 to APP$^{V717F}$ mice, a mouse model of Alzheimer's disease, they can measure levels of Aβ peptides in the circulation that are diagnostic of the levels of amyloid plaques in the brain. Thus, these antibodies are useful not only in conducting assays for circulating Aβ peptides per se, but also for eliciting circulating blood levels which are diagnostic of the amount of amyloid plaque in the brain, and thus useful in identifying individuals in clinical and preclinical stages of Alzheimer's disease. One such antibody, m266, bonds to the mid-region of Aβ peptide.

By "monoclonal antibody that bonds to the mid-region of Aβ peptide" is meant a monoclonal antibody (Mab or Mabs) that binds an amino acid sequence representing an epitope contained between positions 13-28 of Aβ. The entire region need not be targeted. As long as the antibody binds at least an epitope within this region (especially, e.g., including the α-secretase site 16-17 or the site-at which antibody 266 binds), such antibodies are effective in the method of the invention.

By "antibody" is meant a monoclonal antibody per se, or an immunologically effective fragment thereof, such as an $F_{ab}$, $F_{ab'}$, or $F_{(ab')2}$ fragment thereof. In some contexts, herein, fragments will be mentioned specifically for emphasis; nevertheless, it will be understood that regardless of whether fragments are specified, the term "antibody" includes such fragments as well as single-chain forms. As long as the protein retains the ability specifically to bind its intended target, and in this case, to sequester Aβ peptide from its carrier proteins in blood, it is included within the term "antibody." Also included within the definition "antibody" for example, are single chain forms, generally designated $F_v$, regions, of antibodies with this specificity. Preferably, but not necessarily, the antibodies useful in the invention are produced recombinantly, as manipulation of the typically murine or other non-human antibodies with the appropriate specificity is required in order to convert them to humanized form. Antibodies may or may not be glycosylated, though glycosylated antibodies are preferred. Antibodies are properly cross-linked via disulfide bonds, as is well-known.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as gamma, mu, alpha, and lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids.

The variable regions of each light/heavy chain pair form the antibody binding site. Thus, an intact antibody has two binding sites. The chains all exhibit the same general structure of relatively conserved framework regions (FR) joined by three hypervariable regions, also called complementarily determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with well known conventions [Kabat "Sequences of Proteins of Immunological Interest" National Institutes of Health, Bethesda, Md., 1987 and 1991; Chothia, et al., *J. Mol. Bio.* (1987)196:901-917; Chothia, et al., *Nature* (1989) 342:878-883].

As is well understood in the art, monoclonal antibodies can readily be generated with appropriate specificity by standard techniques of immunization of mammals, forming hybridomas from the antibody-producing cells of said mammals or otherwise immortalizing them, and culturing the hybridomas or immortalized cells to assess them for the appropriate specificity. In the present case such antibodies could be generated by immunizing a human, rabbit, rat or mouse, for example, with a peptide representing an epitope encompassing the 13-28 region of the Aβ peptide or an appropriate subregion thereof. Materials for recombinant manipulation can be obtained by retrieving the nucleotide sequences encoding the desired antibody from the hybridoma or other cell that produces it. These nucleotide sequences can then be manipulated to provide them in humanized form, if desired.

It may be desirable to utilize humanized forms of these antibodies in order to elicit the desired circulating levels of the peptides in human subjects. Since the administration is short-term and only for diagnostic purposes, this may not be necessary, but clearly it is preferable to avoid any possibility of an immune response, so the use of humanized forms for this purpose is preferred. Of course, for the performance of the assay of Aβ levels ex vivo (e.g. by ELISA), the murine forms themselves can be used.

By "humanized antibody" is meant an antibody that is composed partially or fully of amino acid sequences derived from a human antibody germline by altering the sequence of an antibody having non-human complementarity determining regions (CDR). The simplest such alteration may consist simply of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. Fully human antibodies are produced in genetically modified mice whose immune systems have been altered to correspond to human immune systems. As mentioned above, it is sufficient for use in the methods of the invention, to employ an immunologically specific fragment of the antibody, including fragments representing single chain forms.

A humanized antibody thus refers to an antibody comprising a human framework, at least one CDR from a non-human antibody, and in which any constant region present is substantially identical to a human inimunoglobulin constant region, i.e., at least about 85-90%, preferably at least 95% identical. Hence, all parts of a humanized antibody, except possibly the CDRs, are substantially identical to corresponding parts of one or more native human immunoglobulin sequences. For example, a humanized immunoglobulin would typically not encompass a chimeric mouse variable region/human constant region antibody.

The design of humanized immunoglobulins may be carried out as follows. When an amino acid falls under the following category, the framework amino acid of a human immunoglobulin to be used (acceptor immunoglobulin) is replaced by a framework amino acid from a CDR-providing non-human immunoglobulin (donor immunoglobulin): (a) the amino acid in the human framework region of the acceptor immunoglobulin is unusual for human immunoglobulin at that position, whereas the corresponding amino acid in the donor immunoglobulin is typical for human immunoglobulin at that position; (b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model [Queen, et al., op. cit., and Co, et al., *Proc. Natl. Acad. Sci. USA* (1991) 88:2869]. When each of the amino acid in the human framework region of the acceptor immunoglobulin and a corresponding amino acid in the donor immunoglobulin is unusual for human immunoglobulin at that position, such an amino acid is replaced by an amino acid typical for human immunoglobulin at that position.

A preferred humanized antibody is a humanized form of mouse antibody 266. The CDRs of humanized 266 have the following amino acid sequences:

```
light chain CDR1:
                                                              (SEQ ID NO: 1)
1               5                    10                   15
Arg Ser Ser Gln Ser Leu Ile Tyr Ser Asp Gly Asn Ala Tyr Leu His light chain CDR2:
                                                              (SEQ ID NO: 2)
1               5
Lys Val Ser Asn Arg Phe Ser
```

-continued light chain CDR3:
(SEQ ID NO: 3)
```
1               5
Ser Gln Ser Thr His Val Pro Trp Thr
``` heavy chain CDR1:
(SEQ ID NO: 4)
```
1               5
Arg Tyr Ser Met Ser
``` heavy chain CDR2:
(SEQ ID NO: 5)
```
 1              5                   10                  15
Gln Ile Asn Ser Val Gly Asn Ser Thr Tyr Tyr Pro Asp Thr Val Lys Gly
and,
``` heavy chain CDR3:
(SEQ ID NO: 6)
```
1
Gly Asp Tyr.
```

A preferred light chain variable region of a humanized antibody of the present invention has the following amino acid sequence, in which the framework originated from human germline Vk segments DPK18 and J segment Jk1, with several amino acid substitutions to the consensus amino acids in the same human V subgroup to reduce potential immunogenicity:

(SEQ ID NO: 7)
```
1               5                   10                  15
Asp Xaa Val Met Thr Gln Xaa Pro Leu Ser Leu Pro Val Xaa Xaa 20                  25                  30
Gly Gln Pro Ala Ser Ile Ser Cys Arg Ser Ser Gln Ser Leu Xaa 35                  40                  45
Tyr Ser Asp Gly Asn Ala Tyr Leu His Trp Phe Leu Gln Lys Pro 50                  55                  60
Gly Gln Ser Pro Xaa Leu Leu Ile Tyr Lys Val Ser Asn Arg Phe 65                  70                  75
Ser Gly Val Pro Asp Arg Phe Ser Gly Ser Gly Ser Gly Thr Asp 80                  85                  90
Phe Thr Leu Lys Ile Ser Arg Val Glu Ala Glu Asp Xaa Gly Val 95                  100                 105
Tyr Tyr Cys Ser Gln Ser Thr His Val Pro Trp Thr Phe Gly Xaa

110
Gly Thr Xaa Xaa Glu Ile Lys Arg
``` wherein:
Xaa at position 2 is Val or Ile;
Xaa at position 7 is Ser or Thr;
Xaa at position 14 is Thr or Ser;
Xaa at position 15 is Leu or Pro;
Xaa at position 30 is Ile or Val;
Xaa at position 50 is Arg, Gln, or Lys;
Xaa at position 88 is Val or Leu;
Xaa at position 105 is Gln or Gly;
Xaa at position 108 is Lys or Arg; and
Xaa at position 109 is Val or Leu.

A preferred heavy chain variable region of a humanized antibody of the present invention has the following amino acid sequence, in which the framework originated from human germline VH segments DP53 and J segment JH4, with several amino acid substitutions to the consensus amino acids in the same human subgroup to reduce potential immunogenicity:

(SEQ ID NO: 8)
```
1               5                   10                  15
Xaa Val Gln Leu Val Glu Xaa Gly Gly Gly Leu Val Gln Pro Gly 20                  25                  30
Gly Ser Leu Arg Leu Ser Cys Ala Ala Ser Gly Phe Thr Phe Ser 35                  40                  45
Arg Tyr Ser Met Ser Trp Val Arg Gln Ala Pro Gly Lys Gly Leu 50                  55                  60
Xaa Leu Val Ala Gln Ile Asn Ser Val Gly Asn Ser Thr Tyr Tyr
```

```
                    65                  70                  75
Pro Asp Xaa Val Lys Gly Arg Phe Thr Ile Ser Arg Asp Asn Xaa 80                  85                  90
Xaa Asn Thr Leu Tyr Leu Gln Met Asn Ser Leu Arg Ala Xaa Asp 95                 100                 105
Thr Ala Val Tyr Tyr Cys Ala Ser Gly Asp Tyr Trp Gly Gln Gly

110
Thr Xaa Val Thr Val Ser Ser
``` wherein:
Xaa at position 1 is Glu or Gln;
Xaa at position 7 is Ser or Leu;
Xaa at position 46 is Glu, Val, Asp, or Ser;
Xaa at position 63 is Thr or Ser;
Xaa at position 75 is Ala, Ser, Val, or Thr;
Xaa at position 76 is Lys or Arg;
Xaa at position 89 is Glu or Asp; and
Xaa at position 107 is Leu or Thr.

A particularly preferred light chain variable region of a humanized antibody of the present invention has the following amino acid sequence, in which the framework originated from human germline Vk segments DPK18 and J segment Jk1, with several amino acid substitutions to the consensus amino acids in the same human V subgroup to reduce potential immunogenicity:

```
                                               (SEQ ID NO: 9)
1                   5                   10                  15
Asp Val Val Met Thr Gln Ser Pro Leu Ser Leu Pro Val Thr Leu 20                  25                  30
Gly Gln Pro Ala Ser Ile Ser Cys Arg Ser Ser Gln Ser Leu Ile 35                  40                  45
Tyr Ser Asp Gly Asn Ala Tyr Leu His Trp Phe Leu Gln Lys Pro 50                  55                  60
Gly Gln Ser Pro Arg Leu Leu Ile Tyr Lys Val Ser Asn Arg Phe 65                  70                  75
Ser Gly Val Pro Asp Arg Phe Ser Gly Ser Gly Ser Gly Thr Asp 80                  85                  90
Phe Thr Leu Lys Ile Ser Arg Val Glu Ala Glu Asp Val Gly Val 95                 100                 105
Tyr Tyr Cys Ser Gln Ser Thr His Val Pro Trp Thr Phe Gly Gln

110
Gly Thr Lys Val Glu Ile Lys Arg.
```

A particularly preferred heavy chain variable region of a humanized antibody of the present invention has the following amino acid sequence, in which the framework originated from human germline VH segments DP53 and J segment JH4:

```
                                               (SEQ ID NO: 10)
1                   5                   10                  15
Glu Val Gln Leu Val Glu Ser Gly Gly Gly Leu Val Gln Pro Gly 20                  25                  30
Gly Ser Leu Arg Leu Ser Cys Ala Ala Ser Gly Phe Thr Phe Ser 35                  40                  45
Arg Tyr Ser Met Ser Trp Val Arg Gln Ala Pro Gly Lys Gly Leu 50                  55                  60
Glu Leu Val Ala Gln Ile Asn Ser Val Gly Asn Ser Thr Tyr Tyr
```

-continued

```
                65                  70                  75
Pro Asp Thr Val Lys Gly Arg Phe Thr Ile Ser Arg Asp Asn Ala 80                  85                  90
Lys Asn Thr Leu Tyr Leu Gln Met Asn Ser Leu Arg Ala Glu Asp 95                 100                 105
Thr Ala Val Tyr Tyr Cys Ala Ser Gly Asp Tyr Trp Gly Gln Gly

110
Thr Leu Val Thr Val Ser Ser.
```

A preferred light chain for a humanized antibody of the present invention has the amino acid sequence:

```
                                                (SEQ ID NO: 11)
1                5                  10                  15
Asp Val Val Met Thr Gln Ser Pro Leu Ser Leu Pro Val Thr Leu 20                  25                  30
Gly Gln Pro Ala Ser Ile Ser Cys Arg Ser Ser Gln Ser Leu Ile 35                  40                  45
Tyr Ser Asp Gly Asn Ala Tyr Leu His Trp Phe Leu Gln Lys Pro 50                  55                  60
Gly Gln Ser Pro Arg Leu Leu Ile Tyr Lys Val Ser Asn Arg Phe 65                  70                  75
Ser Gly Val Pro Asp Arg Phe Ser Gly Ser Gly Ser Gly Thr Asp 80                  85                  90
Phe Thr Leu Lys Ile Ser Arg Val Glu Ala Glu Asp Val Gly Val 95                 100                 105
Tyr Tyr Cys Ser Gln Ser Thr His Val Pro Trp Thr Phe Gly Gln 110                 115                 120
Gly Thr Lys Val Glu Ile Lys Arg Thr Val Ala Ala Pro Ser Val 125                 130                 135
Phe Ile Phe Pro Pro Ser Asp Glu Gln Leu Lys Ser Gly Thr Ala 140                 145                 150
Ser Val Val Cys Leu Leu Asn Asn Phe Tyr Pro Arg Glu Ala Lys 155                 160                 165
Val Gln Trp Lys Val Asp Asn Ala Leu Gln Ser Gly Asn Ser Gln 170                 175                 180
Glu Ser Val Thr Glu Gln Asp Ser Lys Asp Ser Thr Tyr Ser Leu 185                 190                 195
Ser Ser Thr Leu Thr Leu Ser Lys Ala Asp Tyr Glu Lys His Lys 200                 205                 210
Val Tyr Ala Cys Glu Val Thr His Gln Gly Leu Ser Ser Pro Val

215
Thr Lys Ser Phe Asn Arg Gly Glu Cys.
```

A preferred heavy chain for a humanized antibody of the present invention has the amino acid sequence:

(SEQ ID NO: 12)

```
1               5                   10                  15
Glu Val Gln Leu Val Glu Ser Gly Gly Gly Leu Val Gln Pro Gly 20                  25                  30
Gly Ser Leu Arg Leu Ser Cys Ala Ala Ser Gly Phe Thr Phe Ser 35                  40                  45
Arg Tyr Ser Met Ser Trp Val Arg Gln Ala Pro Gly Lys Gly Leu 50                  55                  60
Glu Leu Val Ala Gln Ile Asn Ser Val Gly Asn Ser Thr Tyr Tyr 65                  70                  75
Pro Asp Thr Val Lys Gly Arg Phe Thr Ile Ser Arg Asp Asn Ala 80                  85                  90
Lys Asn Thr Leu Tyr Leu Gln Met Asn Ser Leu Arg Ala Glu Asp 95                  100                 105
Thr Ala Val Tyr Tyr Cys Ala Ser Gly Asp Tyr Trp Gly Gln Gly 110                 115                 120
Thr Leu Val Thr Val Ser Ser Ala Ser Thr Lys Gly Pro Ser Val 125                 130                 135
Phe Pro Leu Ala Pro Ser Ser Lys Ser Thr Ser Gly Gly Thr Ala 140                 145                 150
Ala Leu Gly Cys Leu Val Lys Asp Tyr Phe Pro Glu Pro Val Thr 155                 160                 165
Val Ser Trp Asn Ser Gly Ala Leu Thr Ser Gly Val His Thr Phe 170                 175                 180
Pro Ala Val Leu Gln Ser Ser Gly Leu Tyr Ser Leu Ser Ser Val 185                 190                 195
Val Thr Val Pro Ser Ser Ser Leu Gly Thr Gln Thr Tyr Ile Cys 200                 205                 210
Asn Val Asn His Lys Pro Ser Asn Thr Lys Val Asp Lys Lys Val 215                 220                 225
Glu Pro Lys Ser Cys Asp Lys Thr His Thr Cys Pro Pro Cys Pro 230                 235                 240
Ala Pro Glu Leu Leu Gly Gly Pro Ser Val Phe Leu Phe Pro Pro 245                 250                 255
Lys Pro Lys Asp Thr Leu Met Ile Ser Arg Thr Pro Glu Val Thr 260                 265                 270
Cys Val Val Val Asp Val Ser His Glu Asp Pro Glu Val Lys Phe 275                 280                 285
Asn Trp Tyr Val Asp Gly Val Glu Val His Asn Ala Lys Thr Lys 290                 295                 300
Pro Arg Glu Glu Gln Tyr Asn Ser Thr Tyr Arg Val Val Ser Val 305                 310                 315
Leu Thr Val Leu His Gln Asp Trp Leu Asn Gly Lys Glu Tyr Lys 320                 325                 330
Cys Lys Val Ser Asn Lys Ala Leu Pro Ala Pro Ile Glu Lys Thr 335                 340                 345
Ile Ser Lys Ala Lys Gly Gln Pro Arg Glu Pro Gln Val Tyr Thr 350                 355                 360
Leu Pro Pro Ser Arg Asp Glu Leu Thr Lys Asn Gln Val Ser Leu 365                 370                 375
Thr Cys Leu Val Lys Gly Phe Tyr Pro Ser Asp Ile Ala Val Glu 380                 385                 390
Trp Glu Ser Asn Gly Gln Pro Glu Asn Asn Tyr Lys Thr Thr Pro
```

-continued

```
                395                 400                 405
Pro Val Leu Asp Ser Asp Gly Ser Phe Phe Leu Tyr Ser Lys Leu 410                 415                 420
Thr Val Asp Lys Ser Arg Trp Gln Gln Gly Asn Val Phe Ser Cys 425                 430                 435
Ser Val Met His Glu Ala Leu His Asn His Tyr Thr Gln Lys Ser

440
Leu Ser Leu Ser Pro Gly Lys.
```

Other sequences are possible for the light and heavy chains for the humanized antibodies of the present invention and for humanized 266. The immunoglobulins can have two pairs of light chain/heavy chain complexes, at least one chain comprising one or more mouse complementarity determining regions functionally joined to human framework region segments.

Starting at position 56 of the heavy chain variable region, both m266 and humanized 266 contain the sequence Asn-Ser-Thr. This sequence is an example of the Asn-X-Ser/Thr signal for N-linked glycosylation, wherein the Asn is the site of attachment of N-linked glycosyl chains. Both m266 and humanized 266 are extensively glycosylated at this site. Quite unpredictably and advantageously, the affinity of humanized 266 that is deglycosylated in the heavy chain CDR2 for Aβ peptide is markedly higher than that of humanized 266. The heavy chain CDR2 of deglycosylated humanized 266 has the following amino acid sequences:

```
heavy chain CDR2:
                                              (SEQ ID NO: 13)
1               5                   10                  15
Gln Ile Asn Ser Val Gly Xaa Xaa Xaa Tyr Tyr Pro Asp Thr Val Lys Gly
``` wherein:

Xaa at position 7 is any amino acid, provided that if Xaa at position 8 is neither Asp nor Pro and Xaa at position 9 is Ser or Thr, then Xaa at position 7 is not Asn;

Xaa at position 8 is any amino acid, provided that if Xaa at position 7 is Asn and Xaa at position 9 is Ser or Thr, then Xaa at position 8 is Asp or Pro; and Xaa at position 9 is any amino acid, provided that if Xaa at position 7 is Asn and Xaa at position 8 is neither Asp nor Pro, then Xaa at position 9 is neither Ser nor Thr;

By "any amino acid" is meant any naturally-occurring amino acid. Preferred naturally-occurring amino acids are Ala, Cys, Asp, Glu, Phe, Gly, His, Ile, Lys, Leu, Met, Asn, Pro, Gln, Arg, Ser, Thr, Val, Trp, and Tyr.

A preferred deglycosylated humanized antibody is a humanized form of m266, wherein the deglycosylated heavy chain CDR2 is SEQ ID NO:13, wherein:

Xaa at position 7 of SEQ ID NO:13 is selected from the group consisting of Ala, Cys, Asp, Glu, Phe, Gly, His, Ile, Lys, Leu, Met, Asn, Pro, Gln, Arg, Ser, Thr, Val, Trp, and Tyr, provided that if Xaa at position 8 is neither Asp nor Pro and Xaa at position 9 is Ser or Thr, then Xaa at position 7 is not Asn;

Xaa at position 8 of SEQ ID NO:13 is selected from the group consisting of Ala, Cys, Asp, Glu, Phe, Gly, His, Ile, Lys, Leu, Met, Asn, Pro, Gln, Arg, Ser, Thr, Val, Trp, and Tyr, provided that if Xaa at position 7 is Asn and Xaa at position 9 is Ser or Thr, then Xaa at position 8 is Asp or Pro; and Xaa at position 9 of SEQ ID NO:13 is selected from the group consisting of Ala, Cys, Asp, Glu, Phe, Gly, His, Ile, Lys, Leu, Met, Asn, Pro, Gln, Arg, Ser, Thr, Val, Trp, and Tyr, provided that if Xaa at position 7 is Asn and Xaa at position 8 is neither Asp nor Pro, then Xaa at position 9 is neither Ser nor Thr.

A preferred heavy chain variable region of a deglycosylated humanized antibody of the present invention has the following amino acid sequence, in which the framework originated from human germline VH segment DP53 and J segment JH4, with several amino acid substitutions to the consensus amino acids in the same human subgroup to reduce potential immunogenicity and wherein the N-glycosylation site in heavy chain CDR2 is modified so that it cannot be N-glycosylated:

```
                                                          (SEQ ID NO: 14)
1                   5                       10                        15
Xaa Val Gln Leu Val Glu Xaa Gly Gly Gly Leu Val Gln Pro Gly 20                      25                        30
Gly Ser Leu Arg Leu Ser Cys Ala Ala Ser Gly Phe Thr Phe Ser 35                      40                        45
Arg Tyr Ser Met Ser Trp Val Arg Gln Ala Pro Gly Lys Gly Leu 50                      55                        60
Xaa Leu Val Ala Gln Ile Asn Ser Val Gly Xaa Xaa Xaa Tyr Tyr 65                      70                        75
Pro Asp Xaa Val Lys Gly Arg Phe Thr Ile Ser Arg Asp Asn Xaa 80                      85                        90
```

-continued
```
Xaa Asn Thr Leu Tyr Leu Gln Met Asn Ser Leu Arg Ala Xaa Asp 95                  100                 105
Thr Ala Val Tyr Tyr Cys Ala Ser Gly Asp Tyr Trp Gly Gln Gly 110
Thr Xaa Val Thr Val Ser Ser
``` wherein:
Xaa at position 1 is Glu or Gln;
Xaa at position 7 is Ser or Leu;
Xaa at position 46 is Glu, Val, Asp, or Ser;
Xaa at position 56 is any amino acid, provided that if Xaa at position 57 is neither Asp nor Pro and Xaa at position 59 is Ser or Thr, then Xaa at position 56 is not Asn;
Xaa at position 57 is any amino acid, provided that if Xaa at position 56 is Asn and Xaa at position 58 is Ser or Thr, then Xaa at position 57 is Asp or Pro; and
Xaa at position 58 is any amino acid, provided that if Xaa at position 56 is Asn and Xaa at position 57 is neither Asp nor Pro, then Xaa at position 58 is neither Ser nor Thr
Xaa at position 63 is Thr or Ser;
Xaa at position 75 is Ala, Ser, Val, or Thr;
Xaa at position 76 is Lys or Arg;
Xaa at position 89 is Glu or Asp; and
Xaa at position 107 is Leu or Thr.

A particularly preferred heavy chain variable region of a deglycosylated humanized antibody of the present invention has the following amino acid sequence, in which the framework originated from human germline VH segment DP53 and J segment JH4 and wherein the N-glycosylation site in heavy chain CDR2 is modified so that it cannot be N-glycosylated:

```
                                        (SEQ ID NO: 15)
1               5                   10                  15
Glu Val Gln Leu Val Glu Ser Gly Gly Gly Leu Val Gln Pro Gly 20                  25                  30
Gly Ser Leu Arg Leu Ser Cys Ala Ala Ser Gly Phe Thr Phe Ser 35                  40                  45
Arg Tyr Ser Met Ser Trp Val Arg Gln Ala Pro Gly Lys Gly Leu 50                  55                  60
Glu Leu Val Ala Gln Ile Asn Ser Val Gly Xaa Xaa Xaa Tyr Tyr 65                  70                  75
Pro Asp Thr Val Lys Gly Arg Phe Thr Ile Ser Arg Asp Asn Ala 80                  85                  90
Lys Asn Thr Leu Tyr Leu Gln Met Asn Ser Leu Arg Ala Glu Asp 95                  100                 105
Thr Ala Val Tyr Tyr Cys Ala Ser Gly Asp Tyr Trp Gly Gln Gly

110
Thr Leu Val Thr Val Ser Ser.
``` wherein:
Xaa at position 56 is any amino acid, provided that if Xaa at position 57 is neither Asp nor Pro and Xaa at position 59 is Ser or Thr, then Xaa at position 56 is not Asn;
Xaa at position 57 is any amino acid, provided that if Xaa at position 56 is Asn and Xaa at position 58 is Ser or Thr, then Xaa at position 57 is Asp or Pro; and
Xaa at position 58 is any amino acid, provided that if Xaa at position 56 is Asn and Xaa at position 57 is neither Asp nor Pro, then Xaa at position 58 is neither Ser nor Thr.

A preferred heavy chain for a deglycosylated humanized antibody of the present invention, wherein the N-glycosylation site in heavy chain CDR2 is modified so that it cannot be N-glycosylated, has the amino acid sequence:

(SEQ ID NO: 16)

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
        20                  25                  30

Arg Tyr Ser Met Ser Trp Val Arg Gln Ala Pro Gly Lys Gly Leu
            35                  40                  45

Glu Leu Val Ala Gln Ile Asn Ser Val Gly Xaa Xaa Xaa Tyr Tyr
        50                  55                  60

Pro Asp Thr Val Lys Gly Arg Phe Thr Ile Ser Arg Asp Asn Ala
            65                  70                  75

Lys Asn Thr Leu Tyr Leu Gln Met Asn Ser Leu Arg Ala Glu Asp
        80                  85                  90

Thr Ala Val Tyr Tyr Cys Ala Ser Gly Asp Tyr Trp Gly Gln Gly
            95                  100                 105

Thr Leu Val Thr Val Ser Ser Ala Ser Thr Lys Gly Pro Ser Val
        110                 115                 120

Phe Pro Leu Ala Pro Ser Ser Lys Ser Thr Ser Gly Gly Thr Ala
            125                 130                 135

Ala Leu Gly Cys Leu Val Lys Asp Tyr Phe Pro Glu Pro Val Thr
        140                 145                 150

Val Ser Trp Asn Ser Gly Ala Leu Thr Ser Gly Val His Thr Phe
            155                 160                 165

Pro Ala Val Leu Gln Ser Ser Gly Leu Tyr Ser Leu Ser Ser Val
        170                 175                 180

Val Thr Val Pro Ser Ser Ser Leu Gly Thr Gln Thr Tyr Ile Cys
            185                 190                 195

Asn Val Asn His Lys Pro Ser Asn Thr Lys Val Asp Lys Lys Val
        200                 205                 210

Glu Pro Lys Ser Cys Asp Lys Thr His Thr Cys Pro Pro Cys Pro
            215                 220                 225

Ala Pro Glu Leu Leu Gly Gly Pro Ser Val Phe Leu Phe Pro Pro
        230                 235                 240

Lys Pro Lys Asp Thr Leu Met Ile Ser Arg Thr Pro Glu Val Thr
            245                 250                 255

Cys Val Val Val Asp Val Ser His Glu Asp Pro Glu Val Lys Phe
        260                 265                 270

Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys
            305                 310                 315

Cys Lys Val Ser Asn Lys Ala Leu Pro Ala Pro Ile Glu Lys Thr
        320                 325                 330

Ile Ser Lys Ala Lys Gly Gln Pro Arg Glu Pro Gln Val Tyr Thr
            335                 340                 345

Leu Pro Pro Ser Arg Asp Glu Leu Thr Lys Asn Gln Val Ser Leu
        350                 355                 360

Thr Cys Leu Val Lys Gly Phe Tyr Pro Ser Asp Ile Ala Val Glu
            365                 370                 375

Trp Glu Ser Asn Gly Gln Pro Glu Asn Asn Tyr Lys Thr Thr Pro
        380                 385                 390

Pro Val Leu Asp Ser Asp Gly Ser Phe Phe Leu Tyr Ser Lys Leu
            395                 400                 405

-continued

```
                410                 415                 420
Thr Val Asp Lys Ser Arg Trp Gln Gln Gly Asn Val Phe Ser Cys 425                 430                 435
Ser Val Met His Glu Ala Leu His Asn His Tyr Thr Gln Lys Ser

440
Leu Ser Leu Ser Pro Gly Lys
``` wherein:

Xaa at position 56 is any amino acid, provided that if Xaa at position 57 is neither Asp nor Pro and Xaa at position 59 is Ser or Thr, then Xaa at position 56 is not Asn;

Xaa at position 57 is any amino acid, provided that if Xaa at position 56 is Asn and Xaa at position 58 is Ser or Thr, then Xaa at position 57 is Asp or Pro; and Xaa at position 58 is any amino acid, provided that if Xaa at position 56 is Asn and Xaa at position 57 is neither Asp nor Pro, then Xaa at position 58 is neither Ser nor Thr.

Preferred deglycosylated 266 antibodies having the heavy variable region according to SEQ ID NO:14, SEQ ID NO:15, and SEQ ID NO:16 are those wherein:

Xaa at position 56 is selected from the group consisting of Ala, Gly, His, Asn, Gln, Ser, and Thr, provided that if Xaa at position 58 is Ser or Thr, then Xaa at position 56 is not Asn;

Xaa at position 57 is selected from the group consisting of Ala, Gly, His, Asn, Gln, Ser, and Thr; and Xaa at position 58 is selected from the group consisting of Ala, Gly, His, Asn, Gln, Ser, and Thr, provided that if Xaa at position 56 is Asn, then Xaa at position 58 is neither Ser nor Thr.

Preferred sequences for CDR2 (positions 56, 57, and 58) of the heavy chain SEQ ID NO:14, SEQ ID NO:15, and SEQ ID NO:16 include those in which only a single amino acid is changed, those in which only two amino acids are changed, or all three are changed. It is preferred to replace Asn at position 56. It is preferred to replace Thr at position 58 with an amino acid other than Ser. It is preferred to not destroy the N-glycosylation site in the CDR2 of the 266 heavy chain by replacing Ser at position 57 with Pro or Asp. Conservative substitutions at one, two, or all three positions are preferred. The most preferred species are those in which Asn at position 56 is replaced with Ser or Thr. Particularly preferred antibodies are those in which Ser or Thr is at position 56, Ser is at position 57, and Thr is at position 58 of SEQ ID NO:14, SEQ ID NO:15, or SEQ ID NO:16.

Especially preferred deglycosylated species are antibodies comprising a light chain of SEQ ID NO:11 and a heavy chain of SEQ ID NO:16, wherein in SEQ ID NO:16, Xaa at position 56 is Ser, Xaa at position 57 is Ser, and Xaa at position 58 is Thr ("N56S"), or wherein in SEQ ID NO:16, Xaa at position 56 is Thr, Xaa at position 57 is Ser, and Xaa at position 58 is Thr ("N56T").

Production of the antibodies useful in the invention typically involves recombinant techniques, as is described in PCT/US01/06191 cited above and incorporated herein by reference.

The antibodies (including immnunologically reactive fragments) are administered to a subject to be evaluated for conditions associated with Aβ deposits such as clinical or preclinical Alzheimer's disease, or clinical or preclinical amyloid angiopathy, using standard administration techniques, preferably peripherally (i.e. not by administration into the central nervous system) by intravenous, intraperitoneal, subcutaneous, pulmonary, transdermal, intramuscular, intranasal, buccal, sublingual, or suppository administration.

The compositions for administration are designed to be appropriate for the selected mode of administration, and pharmaceutically acceptable excipients such as dispersing agents, buffers, surfactants, preservatives, solubilizing agents, isotonicity agents, stabilizing agents and the like are used as appropriate. Remington's Pharmaceutical Sciences, Mack Publishing Co., Easton Pa., latest edition, incorporated herein by reference, provides a compendium of formulation techniques as are generally known to practitioners. It may be particularly useful to alter the solubility characteristics of the antibodies of the invention, making them more lipophilic, for example, by encapsulating them in liposomes or by blocking polar groups.

Peripheral systemic delivery by intravenous or intraperitoneal or subcutaneous injection is preferred. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

The concentration of the humanized antibody in formulations from as low as about 0.1% to as much as 15 or 20% by weight and will be selected primarily based on fluid volumes, viscosities, and so forth, in accordance with the particular mode of administration selected. Thus, a typical composition for injection could be made up to contain 1 mL sterile buffered water of phosphate buffered saline and 1-1000 mg, preferably 10-100 mg, of the humanized antibody of the present invention. The formulation could be sterile filtered after making the formulation, or otherwise made microbiologically acceptable. A typical composition for intravenous infusion could have volumes between 1-250 mL of fluid, such as sterile Ringer's solution, and 1-100 mg per mL, or more in antibody concentration. Therapeutic agents of the invention can be frozen or lyophilized for storage and reconstituted in a suitable sterile carrier prior to use. Lyophilization and reconstitution can lead to varying degrees of antibody activity loss (e.g. with conventional immune globulins, IgM antibodies tend to have greater activity loss than IgG antibodies). Dosages may have to be adjusted to compensate. The pH of the formulation will be selected to balance antibody stability (chemical and physical) and comfort to the patient when administered. Generally, pH between 4 and 8 is tolerated.

Although the foregoing methods appear the most convenient and most appropriate for administration of proteins such as humanized antibodies, by suitable adaptation, other techniques for administration, such as transdermal administration and oral administration may be employed provided proper formulation is designed.

In addition, it may be desirable to employ controlled release formulations using biodegradable films and matrices, or osmotic mini-pumps, or delivery systems based on dextran beads, alginate, or collagen.

In summary, formulations are available for administering the antibodies of the invention and are well-known in the art and may be chosen from a variety of options.

Typical dosage levels can be optimized using standard clinical techniques and will be dependent on the mode of administration.

After administration of the antibody to the subject, blood samples are withdrawn at periodic intervals over the succeeding minutes, hours, or days. Suitable time periods may be as short as a few minutes, 10 minutes, 30 minutes, or 1 hour, several hours, or days may be allowed to elapse before withdrawal of the blood sample. Measurement after less than 3 hours is preferred. If desired, the plasma fraction can be obtained for ease of analysis. Standard analytic techniques for analysis of the $A\beta_{40}$, $A\beta_{42}$ and the ratio thereof are used. These techniques are described, for example, in U.S. Pat. No. 5,766,846. Any suitable technique for analysis, however, can be employed, such as chromatographic separation, Western blotting, ELISA assays, homogenous assays and the like.

The concentration of the $A\beta_{40}$, $A\beta_{42}$, or their ratio is then compared to these values in a control. Typical controls include individuals known to be free of conditions associated with the amyloid plaques, such as teenagers or very young adults and in addition, age-matched cognitively normal controls are obtained by averaging values from the general population. While some elderly age-matched cognitively normal controls have pre-clinical AD, most do not. Thus, the average values from such a population will be useful and critical to obtain. Design of standard controls is a process that is well known to the ordinary practitioner. Individuals who have elevated levels of the stated peptides or of the ratio of $A\beta_{40}$ to $A\beta_{42}$ as compared to the control values are then identified as having a high likelihood of clinical or preclinical conditions associated with the formation of amyloid plaques.

It may be desirable to package the components for carrying out the assay of the invention into convenient kits. Such kits will include containers such as bottles or vials which contain samples of the antibody to be administered as well as the appropriate reagents for carrying out the assay on the withdrawn blood sample. The kit will also contain instructions for conducting the assay and, optionally, charts of control values.

The following examples are intended to illustrate but not to limit the invention.

The examples hereinbelow employ, among others, a murine monoclonal antibody designated "266" which was originally prepared by immunization with a peptide comprised of residues 13-28 of human Aβpeptide. The antibody was confirmed to immunoreact with this peptide, but had previously been reported to not react with the peptide containing only residues 17-28 of human Aβ peptide, or at any other epitopes within the Aβ peptide. The preparation of this antibody is described in U.S. Pat. No. 5,766,846, incorporated herein by reference. As the examples here describe experiments conducted in murine systems, the use of murine monoclonal antibodies is satisfactory. However, in the treatment methods of the invention intended for human use, humanized forms of the antibodies with the immunospecificity corresponding to that of antibody 266 are preferred.

Example 1

Correlation of Circuiating Peptide Levels with Plaques

A murine model for Alzheimer's disease, APP V717F transgenic mice, was used in this assay. These mice are described by Games, D., et al., *Nature* (1995) 373:523-527; Bales, K. R., et al., *Nature Genet.* (1997) 17:263-264; and by Holtzman, D. M., et al., *Proc. Natl. Acad. Sci. U.S.A.* (2000) 97:2892-2897. In this model, a mutant form of the human APP gene is expressed and results in an early onset form of familial Alzheimer's disease. Although the brains of these mice appear normal initially, Aβ deposition in the form of diffuse and neuritic plaques occurs at 6-15 months, although mice homozygous for the transgene show variability in that at 9-14 months of age, some mice develop Aβ deposits while others do not.

53 homozygous mice at 12 months were used in this study.

Plasma levels of $A\beta_{40}$, $A\beta_{42}$, and $A\beta_{40}/A\beta_{42}$ ratios were measured by ELISA in the plasma of these mice prior to administration of 500 μg of m266 and at various time intervals up to 24 hours after administering this antibody. After 24 hours, the mice were sacrificed, and the amount of Aβ deposition in the brain was assessed in the hippocampus and cortex as described by DeMattos, et al. *Proc. Nat'l. Acad. Sci USA* (2001) 98:8850-8855, and evaluated as a percentage of brain covered by Aβ deposits.

As shown in FIGS. 1A, B and C, if the percentage Aβ coverage due to deposition in the hippocampus is plotted on the x-axis against the levels of the peptides and their ratio in plasma on the y-axis prior to administration of the antibody, no correlation is found. Regardless of whether the percent Aβ deposition was essentially zero (0) or over 75%, the average level of $A\beta_{40}$ was approximately 250 (pg/ml) and of $A\beta_{42}$ approximately 400 (pg/ml). The ratio of $A\beta_{40}$ to $A\beta_{42}$ was thus approximately 0.5-0.6.

Figure 2:
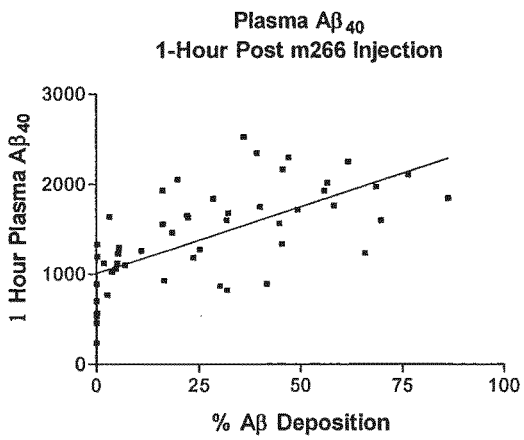
FIGS. 2 A and B are graphs showing plasma $A\beta_{40}$ (FIG. 2A) and plasma $A\beta_{40}/A\beta_{42}$ ratio (FIG. 2B) in transgenic mice one hour after injection of antibody m266, and the significant correlation with brain Aβ deposits.
Figure 2:
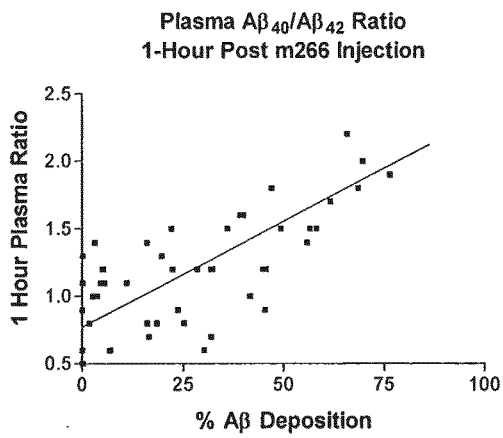

As shown in FIGS. 2 A and B, however, the plasma level of $A\beta_{40}$ strongly correlated with the percentage of Aβ deposition in hippocampus one hour after m266 injection, as did the ratio of $A\beta_{40}$ to $A\beta_{42}$.

Figure 3:
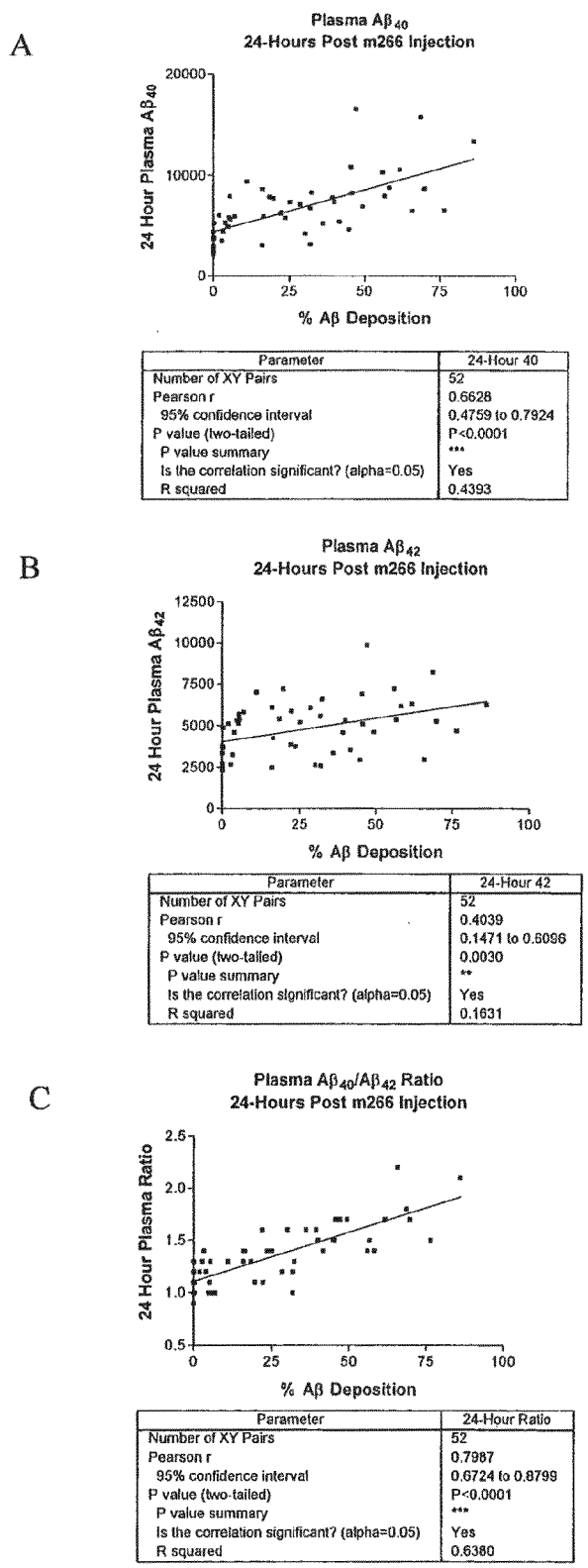
FIGS. 3 A, B and C are graphs showing the significant correlations of the two Aβ peptides (FIGS. 3A and 3B) and their ratio (FIG. 3C) with Aβ peptide deposition in the brain 24 hours after injection with monoclonal antibody m266.

FIGS. 3 A, B and C show similar results obtained 24 hours post injection. The levels obtained of $A\beta_{40}$ and the $A\beta_{40}/A\beta_{42}$ ratio strongly correlated with the % Aβ deposition in hippocampus The $A\beta_{42}$ levels also correlated with % Aβdeposition but not as well as $A\beta_{40}$ levels.

Figure 4:
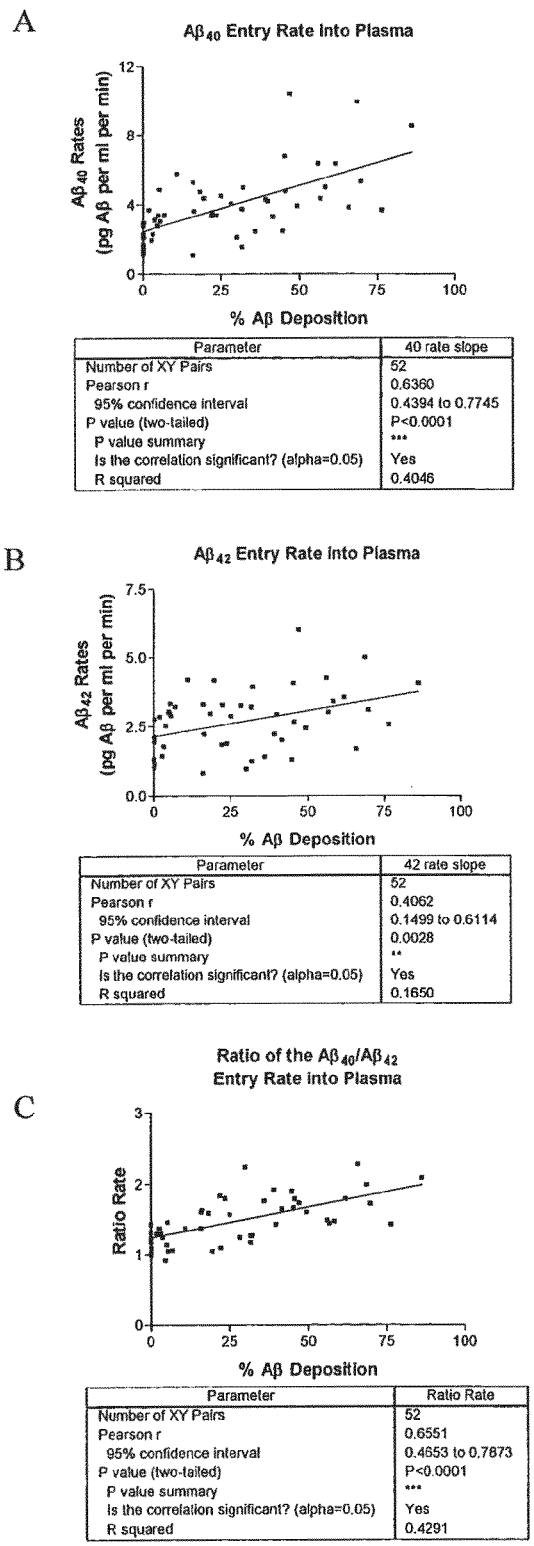
FIGS. 4 A, B and C are graphs showing the significant correlations of entry rates into the circulation of the two Aβ peptides (FIGS. 4A and 4B) and their ratio (FIG. 4C) and Aβ peptide deposition in transgenic mice.

FIGS. 4 A, B and C show analogous results with respect to entry rate of the two Aβ peptides into the plasma and the calculated values for the entry rate as a function of the ratio of these peptides. The best correlations with Aβ deposition were rate of $A\beta_{40}$ entry and the ratio of $A\beta_{40}/A\beta_{42}$.

Figure 5:
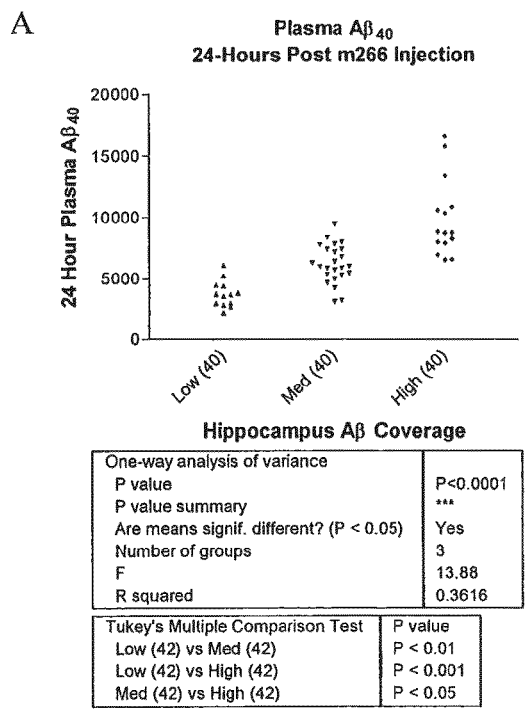
FIGS. 5 A and B are graphs showing an alternative graphical representation of $A\beta_{40}$ levels in the plasma 24 hours (FIG. 5A) and 1 hour (FIG. 5B) after m266 injection correlated with the percentage hippocampus covered by Aβ deposits.
Figure 5:
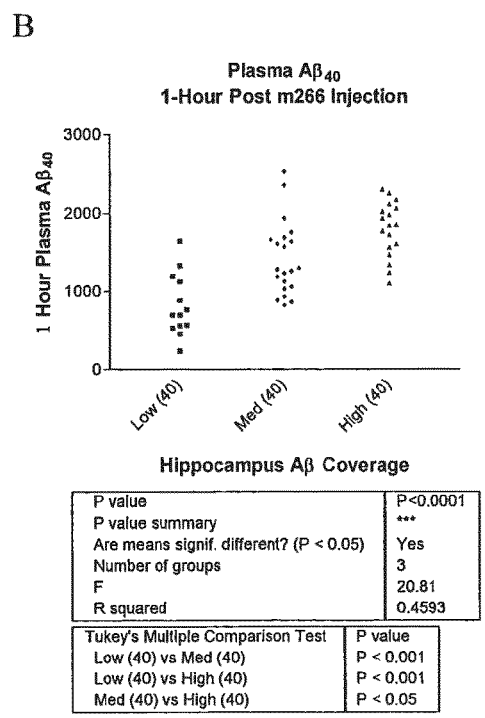

FIGS. 5 A and B show an alternate presentation of the data for plasma levels of $A\beta_{40}$ 24 hours and 1 hour after m266 injection. When the mice were grouped according to low, medium, or high Aβ coverage in the hippocampus, the animals with low Aβ deposition could be completely distinguished from those with high deposition as a function of the level of plasma $A\beta_{40}$.

Example 2

In a study similar to that set forth in Example 1, a cohort of 49 homozygous APP V717F mice were used. Before and after injection of 500 μg IV of m266, plasma samples were obtained at 5 minutes, 1 hour, 3 hours, 6 hours and 24 hours and levels of $A\beta_{40}$ and $A\beta_{42}$ were assessed as described in Example 1. The mice were sacrificed after 24 hours and 1 hemisphere was assessed for the percentage of the area of the hippocampus or cingulate cortex occupied by Aβ peptide (using quantitative Aβ immunofluorescence staining) and the area occupied by amyloid (by thioflavine-S (amyloid) staining). The regions from the other hemisphere were assessed for Aβ peptide by ELISA.

The Pearson correlation coefficient (Pearson r) and significance (P value) were determined between plasma Aβ values (pre and post injection of m266) and hippocampal Aβ or amyloid load using GraphPad Prism software (version 3.00 for Windows, San Diego, USA). Aβ load is defined as the percentage area of the hippocampus covered by Aβ-immunoreactive deposits. Amyloid load is defined as the percentage area of the hippocampus covered by thioflavine-S positive deposits. Correlations were also determined between the plasma Aβ accumulation over 24 hours (area under curve, AUC) and hippocampal Aβ load or amyloid load.

FIG. 6 shown the results obtained. Briefly, it was found that the base line levels (prior to injection) of $A\beta_{40}$, $A\beta_{42}$ and the calculated $A\beta_{40}/_{42}$ ratio prior to injection with m266 did not correlate with percentage Aβ or amyloid deposition. However, following administration of m266, there were significant correlations between plasma $A\beta_{40}$, $A\beta_{42}$, and $A\beta_{40}/_{42}$ ratio with both Aβ and amyloid burden in the hippocampus and cingulate cortex.

Statistical analysis of the results permits accurate prediction of hippocampal Aβ load in these mice based on plasma $A\beta_{40}$ levels 24 hours following m266 injection.

The invention claimed is:

1. A method for diagnosing a condition associated with Aβ deposits in a subject comprising the steps of:
    (a) administering to the subject an amount of an antibody which specifically binds an epitope contained within positions 13-28 of Aβ;
    (b) measuring the level of Aβ$_{40}$ in a blood sample obtained from the subject at a time interval after the administering step; and
    (c) comparing the measured level of Aβ$_{40}$ in the subject with a control value, wherein an altered measured level of Aβ$_{40}$ in the subject as compared to the control value identifies the subject as having a condition associated with Aβ deposits.

2. The method of claim 1, wherein the time interval is less than 1 week.

3. The method of claim 1, wherein the time interval is less than or equal to 24 hours.

4. The method of claim 1, wherein the time interval is less than or equal to 3 hours.

5. The method of claim 1, wherein the subject is human and the antibody is a humanized antibody or an epitope-binding fragment thereof.

6. The method of claim 5, wherein the humanized antibody or epitope-binding fragment thereof comprises a light chain of the sequence given by SEQ ID NO:11 and a heavy chain of the sequence given by SEQ ID NO:12.

7. The method of claim 5, wherein the humanized antibody or epitope-binding fragment thereof comprises a light chain of the sequence given by SEQ ID NO:11 and a heavy chain of the sequence given by SEQ ID NO:16.

8. The method of claim 5, wherein the humanized antibody or epitope-binding fragment thereof comprises a light chain comprising a variable region of the sequence given by SEQ ID NO:7 and a heavy chain comprising a variable region of the sequence given by SEQ ID NO:14.

9. The method of claim 5, wherein the humanized antibody or epitope-binding fragment thereof comprises:
    a. a light chain comprising three light chain complementarity determining regions (CDRs) having the following amino acid sequences:

```
light chain CDR1:
1               5                   10                  15
Arg Ser Ser Gln Ser Leu Ile Tyr Ser Asp Gly Asn Ala Tyr Leu His; (SEQ ID NO: 1)
or 1               5                   10                  15
Arg Ser Ser Gln Ser Leu Val Tyr Ser Asp Gly Asn Ala Tyr Leu His  (SEQ ID NO: 17)

light chain CDR2:
1               5
Lys Val Ser Asn Arg Phe Ser                                      (SEQ ID NO: 2)
and, light chain CDR3:
1               5
Ser Gln Ser Thr His Val Pro Trp Thr                              (SEQ ID NO: 3)
``` and a light chain framework sequence from a humanized immunoglobulin light chain; and
    b. a heavy chain comprising three heavy chain CDRs having the following amino acid sequences:

```
heavy chain CDR1:
1               5
Arg Tyr Ser Met Ser                                              (SEQ ID NO: 4)

heavy chain CDR2:
1               5                   10                  15
Gln Ile Asn Ser Val Gly Asn Ser Thr Tyr Tyr Pro Asp Thr Val Lys Gly; (SEQ ID NO: 5)
or 1               5                   10                  15
Gln Ile Asn Ser Val Gly Asn Ser Thr Tyr Tyr Pro Asp Ser Val Lys Gly  (SEQ ID NO: 18)
and, heavy chain CDR3:
1
Gly Asp Tyr                                                      (SEQ ID NO: 6)
``` and a heavy chain framework sequence from a humanized immunoglobulin heavy chain.

10. The method of claim 1, wherein the antibody is an epitope-binding fragment thereof.

11. The method of claim 1, wherein the antibody is a single-chain antibody.

12. The method of claim 1, wherein the condition associated with Aβ deposits is Down's syndrome, preclinical cerebral amyloid angiopathy, or clinical cerebral amyloid angiopathy.

* * * * *

SEQUENCE LISTING

```
<160> NUMBER OF SEQ ID NOS: 18

<210> SEQ ID NO 1
<211> LENGTH: 16
<212> TYPE: PRT
<213> ORGANISM: Mus sp.
<220> FEATURE:
<221> NAME/KEY: MISC_FEATURE
<222> LOCATION: (1)..(16)
<223> OTHER INFORMATION: Light Chain CDR1

<400> SEQUENCE: 1

Arg Ser Ser Gln Ser Leu Ile Tyr Ser Asp Gly Asn Ala Tyr Leu His
1               5                   10                  15

<210> SEQ ID NO 2
<211> LENGTH: 7
<212> TYPE: PRT
<213> ORGANISM: mus sp.
<220> FEATURE:
<221> NAME/KEY: MISC_FEATURE
<222> LOCATION: (1)..(7)
<223> OTHER INFORMATION: Light Chain CDR2

<400> SEQUENCE: 2

Lys Val Ser Asn Arg Phe Ser
1               5

<210> SEQ ID NO 3
<211> LENGTH: 9
<212> TYPE: PRT
<213> ORGANISM: mus sp.
<220> FEATURE:
<221> NAME/KEY: MISC_FEATURE
<222> LOCATION: (1)..(9)
<223> OTHER INFORMATION: Light Chain CDR3

<400> SEQUENCE: 3

Ser Gln Ser Thr His Val Pro Trp Thr
1               5

<210> SEQ ID NO 4
<211> LENGTH: 5
<212> TYPE: PRT
<213> ORGANISM: mus sp.
<220> FEATURE:
<221> NAME/KEY: MISC_FEATURE
<222> LOCATION: (1)..(5)
<223> OTHER INFORMATION: Heavy Chain CDR1

<400> SEQUENCE: 4

Arg Tyr Ser Met Ser
1               5
```

-continued

```
<210> SEQ ID NO 5
<211> LENGTH: 17
<212> TYPE: PRT
<213> ORGANISM: mus sp.
<220> FEATURE:
<221> NAME/KEY: MISC_FEATURE
<222> LOCATION: (1)..(16)
<223> OTHER INFORMATION: Heavy Chain CDR2

<400> SEQUENCE: 5

Gln Ile Asn Ser Val Gly Asn Ser Thr Tyr Tyr Pro Asp Thr Val Lys
1               5                   10                  15

Gly

<210> SEQ ID NO 6
<211> LENGTH: 3
<212> TYPE: PRT
<213> ORGANISM: mus sp.
<220> FEATURE:
<221> NAME/KEY: MISC_FEATURE
<222> LOCATION: (1)..(3)
<223> OTHER INFORMATION: Heavy Chain CDR3

<400> SEQUENCE: 6

Gly Asp Tyr
1

<210> SEQ ID NO 7
<211> LENGTH: 113
<212> TYPE: PRT
<213> ORGANISM: artificial sequence
<220> FEATURE:
<223> OTHER INFORMATION: humanized antibody
<220> FEATURE:
<221> NAME/KEY: MISC_FEATURE
<222> LOCATION: (1)..(113)
<223> OTHER INFORMATION: Humanized Antibody Light Chain Variable Region
<220> FEATURE:
<221> NAME/KEY: MISC_FEATURE
<222> LOCATION: (2)..(2)
<223> OTHER INFORMATION: Xaa at position 2 is Val or Ile
<220> FEATURE:
<221> NAME/KEY: MISC_FEATURE
<222> LOCATION: (7)..(7)
<223> OTHER INFORMATION: Xaa at position 7 is Ser or Thr
<220> FEATURE:
<221> NAME/KEY: MISC_FEATURE
<222> LOCATION: (14)..(14)
<223> OTHER INFORMATION: Xaa at position 14 is Thr or Ser
<220> FEATURE:
<221> NAME/KEY: MISC_FEATURE
<222> LOCATION: (15)..(15)
<223> OTHER INFORMATION: Xaa at position 15 is Leu or Pro
<220> FEATURE:
<221> NAME/KEY: MISC_FEATURE
<222> LOCATION: (30)..(30)
<223> OTHER INFORMATION: Xaa at position 30 is Ile or Val
<220> FEATURE:
<221> NAME/KEY: MISC_FEATURE
<222> LOCATION: (50)..(50)
<223> OTHER INFORMATION: Xaa at position 50 is Arg, Gln, or Lys
<220> FEATURE:
<221> NAME/KEY: MISC_FEATURE
<222> LOCATION: (88)..(88)
<223> OTHER INFORMATION: Xaa at position 88 is Val or Leu
<220> FEATURE:
<221> NAME/KEY: MISC_FEATURE
<222> LOCATION: (105)..(105)
<223> OTHER INFORMATION: Xaa at position 105 is Gln or Gly
<220> FEATURE:
<221> NAME/KEY: MISC_FEATURE
<222> LOCATION: (108)..(108)
<223> OTHER INFORMATION: Xaa at position 108 is Lys or Arg
<220> FEATURE:
<221> NAME/KEY: MISC_FEATURE
```

<222> LOCATION: (109)..(109)
<223> OTHER INFORMATION: Xaa at position 109 is Val or Leu

<400> SEQUENCE: 7

Asp Xaa Val Met Thr Gln Xaa Pro Leu Ser Leu Pro Val Xaa Xaa Gly
1               5                   10                  15

Gln Pro Ala Ser Ile Ser Cys Arg Ser Ser Gln Ser Leu Xaa Tyr Ser
            20                  25                  30

Asp Gly Asn Ala Tyr Leu His Trp Phe Leu Gln Lys Pro Gly Gln Ser
        35                  40                  45

Pro Xaa Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Ser Gln Ser
                85                  90                  95

Thr His Val Pro Trp Thr Phe Gly Xaa Gly Thr Xaa Xaa Glu Ile Lys
            100                 105                 110

Arg

<210> SEQ ID NO 8
<211> LENGTH: 112
<212> TYPE: PRT
<213> ORGANISM: artificial sequence
<220> FEATURE:
<223> OTHER INFORMATION: Humanized antibody
<220> FEATURE:
<221> NAME/KEY: MISC_FEATURE
<222> LOCATION: (1)..(112)
<223> OTHER INFORMATION: Humanized Antibody Heavy Chain Variable Region
<220> FEATURE:
<221> NAME/KEY: MISC_FEATURE
<222> LOCATION: (1)..(1)
<223> OTHER INFORMATION: Xaa at position 1 is Glu or Gln
<220> FEATURE:
<221> NAME/KEY: MISC_FEATURE
<222> LOCATION: (7)..(7)
<223> OTHER INFORMATION: Xaa at position 7 is Ser or Leu
<220> FEATURE:
<221> NAME/KEY: MISC_FEATURE
<222> LOCATION: (46)..(46)
<223> OTHER INFORMATION: Xaa at position 46 is Glu, Val, Asp, or Ser
<220> FEATURE:
<221> NAME/KEY: MISC_FEATURE
<222> LOCATION: (63)..(63)
<223> OTHER INFORMATION: Xaa at position 63 is Thr or Ser
<220> FEATURE:
<221> NAME/KEY: MISC_FEATURE
<222> LOCATION: (75)..(75)
<223> OTHER INFORMATION: Xaa at position 75 is Ala, Ser, Val, or Thr
<220> FEATURE:
<221> NAME/KEY: MISC_FEATURE
<222> LOCATION: (76)..(76)
<223> OTHER INFORMATION: Xaa at position 76 is Lys or Arg
<220> FEATURE:
<221> NAME/KEY: MISC_FEATURE
<222> LOCATION: (89)..(89)
<223> OTHER INFORMATION: Xaa at position 89 is Glu or Asp
<220> FEATURE:
<221> NAME/KEY: MISC_FEATURE
<222> LOCATION: (107)..(107)
<223> OTHER INFORMATION: Xaa at position 107 is Leu or Thr

<400> SEQUENCE: 8

Xaa Val Gln Leu Val Glu Xaa Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

```
Ser Met Ser Trp Val Arg Gln Ala Pro Gly Lys Gly Leu Xaa Leu Val
        35                  40                  45

Ala Gln Ile Asn Ser Val Gly Asn Ser Thr Tyr Tyr Pro Asp Xaa Val
    50                  55                  60

Lys Gly Arg Phe Thr Ile Ser Arg Asp Asn Xaa Xaa Asn Thr Leu Tyr
65                  70                  75                  80

Leu Gln Met Asn Ser Leu Arg Ala Xaa Asp Thr Ala Val Tyr Tyr Cys
                85                  90                  95

Ala Ser Gly Asp Tyr Trp Gly Gln Gly Thr Xaa Val Thr Val Ser Ser
            100                 105                 110

<210> SEQ ID NO 9
<211> LENGTH: 113
<212> TYPE: PRT
<213> ORGANISM: artificial sequence
<220> FEATURE:
<223> OTHER INFORMATION: Humanized antibody
<220> FEATURE:
<221> NAME/KEY: MISC_FEATURE
<222> LOCATION: (1)..(113)
<223> OTHER INFORMATION: Humanized Antibody Light Chain Variable Region

<400> SEQUENCE: 9

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
            20                  25                  30

Asp Gly Asn Ala Tyr Leu His Trp Phe Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg

<210> SEQ ID NO 10
<211> LENGTH: 112
<212> TYPE: PRT
<213> ORGANISM: artificial sequence
<220> FEATURE:
<223> OTHER INFORMATION: Humanized Antibody
<220> FEATURE:
<221> NAME/KEY: MISC_FEATURE
<222> LOCATION: (1)..(112)
<223> OTHER INFORMATION: Humanized Antibody Heavy Chain Variable Region

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Glu Leu Val
        35                  40                  45

Ala Gln Ile Asn Ser Val Gly Asn Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Ser Gly Asp Tyr Trp Gln Gly Thr Leu Val Thr Val Ser Ser
            100                 105                 110

<210> SEQ ID NO 11
<211> LENGTH: 219
<212> TYPE: PRT
<213> ORGANISM: artificial sequence
<220> FEATURE:
<223> OTHER INFORMATION: Humanized antibody
<220> FEATURE:
<221> NAME/KEY: MISC_FEATURE
<222> LOCATION: (1)..(219)
<223> OTHER INFORMATION: Humanized Antibody Light Chain

<400> SEQUENCE: 11

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
            20                  25                  30

Asp Gly Asn Ala Tyr Leu His Trp Phe Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 12
<211> LENGTH: 442
<212> TYPE: PRT
<213> ORGANISM: artificial sequence
<220> FEATURE:
<223> OTHER INFORMATION: Humanized antibody
<220> FEATURE:
<221> NAME/KEY: MISC_FEATURE
<222> LOCATION: (1)..(442)
<223> OTHER INFORMATION: Humanized Antibody Heavy Chain

<400> SEQUENCE: 12

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Glu Leu Val
        35                  40                  45

Ala Gln Ile Asn Ser Val Gly Asn Ser Thr Tyr Tyr Pro Asp Thr Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Gly Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440
```

```
<210> SEQ ID NO 13
<211> LENGTH: 16
<212> TYPE: PRT
<213> ORGANISM: mus variant
<220> FEATURE:
<221> NAME/KEY: MISC_FEATURE
<222> LOCATION: (1)..(16)
<223> OTHER INFORMATION: Heavy Chain CDR2
<220> FEATURE:
<221> NAME/KEY: MISC_FEATURE
<222> LOCATION: (7)..(7)
<223> OTHER INFORMATION: Xaa at position 7 is any amino acid, provided
      that Xaa at position 8 is neither Asp nor Pro and Xaa at position
      9 is Ser or Thr, then Xaa at position 7 is not Asn
<220> FEATURE:
<221> NAME/KEY: MISC_FEATURE
<222> LOCATION: (8)..(8)
<223> OTHER INFORMATION: Xaa at position 8 is any amino acid, provided
      that Xaa at position 7 is Asn and Xaa at position 9 is Ser or Thr,
      then Xaa at position 8 is Asp or Pro
<220> FEATURE:
<221> NAME/KEY: MISC_FEATURE
<222> LOCATION: (9)..(9)
<223> OTHER INFORMATION: Xaa at position 9 is any amino acid, provided
      that Xaa at position 7 is Asn and Xaa at position 8 is neither Asp
      nor Pro, then Xaa at position 9 is neither Ser nor Thr

<400> SEQUENCE: 13

Gln Ile Asn Ser Val Gly Xaa Xaa Xaa Tyr Tyr Pro Asp Thr Val Lys
1               5                   10                  15

<210> SEQ ID NO 14
<211> LENGTH: 112
<212> TYPE: PRT
<213> ORGANISM: artificial sequence
<220> FEATURE:
<223> OTHER INFORMATION: humanized antibody
<220> FEATURE:
<221> NAME/KEY: MISC_FEATURE
<222> LOCATION: (1)..(112)
<223> OTHER INFORMATION: Deglycosylated Humanized Antibody Heavy Chain
      Variable Region
<220> FEATURE:
<221> NAME/KEY: MISC_FEATURE
<222> LOCATION: (1)..(1)
<223> OTHER INFORMATION: Xaa at position 1 is Glu or Gln
<220> FEATURE:
<221> NAME/KEY: MISC_FEATURE
<222> LOCATION: (7)..(7)
<223> OTHER INFORMATION: Xaa at position 7 is Ser or Leu
<220> FEATURE:
<221> NAME/KEY: MISC_FEATURE
<222> LOCATION: (46)..(46)
<223> OTHER INFORMATION: Xaa at position 46 is Glu, Val, Asp, or Ser
<220> FEATURE:
<221> NAME/KEY: MISC_FEATURE
<222> LOCATION: (56)..(56)
<223> OTHER INFORMATION: Xaa at position 56 is any amino acid, provided
      that if Xaa at position 57 is neither Asp nor Pro and Xaa at
      position 58 is Ser or Thr, then Xaa at position 56 is not Asn
<220> FEATURE:
<221> NAME/KEY: MISC_FEATURE
<222> LOCATION: (57)..(57)
<223> OTHER INFORMATION: Xaa at position 57 is any amino acid, provided
      that if Xaa at position 56 is Asn and Xaa at position 58 is Ser or
      Thr, then Xaa at position 57 is Asp or Pro
<220> FEATURE:
<221> NAME/KEY: MISC_FEATURE
<222> LOCATION: (58)..(58)
<223> OTHER INFORMATION: Xaa at position 58 is any amino acid, provided
      that if Xaa at position 56 is Asn and Xaa at position 57 is
      neither Asp nor Pro, then Xaa at position 58 is neither Ser nor
      Thr
<220> FEATURE:
<221> NAME/KEY: MISC_FEATURE
<222> LOCATION: (63)..(63)
```

```
<223> OTHER INFORMATION: Xaa at position 63 is Thr or Ser
<220> FEATURE:
<221> NAME/KEY: MISC_FEATURE
<222> LOCATION: (75)..(75)
<223> OTHER INFORMATION: Xaa at position 75 is Ala, Ser, Val, or Thr
<220> FEATURE:
<221> NAME/KEY: MISC_FEATURE
<222> LOCATION: (76)..(76)
<223> OTHER INFORMATION: Xaa at position 76 is Lys or Arg
<220> FEATURE:
<221> NAME/KEY: MISC_FEATURE
<222> LOCATION: (89)..(89)
<223> OTHER INFORMATION: Xaa at position 89 is Glu or Asp
<220> FEATURE:
<221> NAME/KEY: MISC_FEATURE
<222> LOCATION: (107)..(107)
<223> OTHER INFORMATION: Xaa at position 107 is Leu or Thr

<400> SEQUENCE: 14

Xaa Val Gln Leu Val Glu Xaa Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Xaa Leu Val
        35                  40                  45

Ala Gln Ile Asn Ser Val Gly Xaa Xaa Xaa Tyr Tyr Pro Asp Xaa Val
    50                  55                  60

Lys Gly Arg Phe Thr Ile Ser Arg Asp Asn Xaa Asn Thr Leu Tyr
65                  70                  75                  80

Leu Gln Met Asn Ser Leu Arg Ala Xaa Asp Thr Ala Val Tyr Tyr Cys
            85                  90                  95

Ala Ser Gly Asp Tyr Trp Gly Gln Gly Thr Xaa Val Thr Val Ser Ser
        100                 105                 110

<210> SEQ ID NO 15
<211> LENGTH: 112
<212> TYPE: PRT
<213> ORGANISM: artificial sequence
<220> FEATURE:
<223> OTHER INFORMATION: humanized antibody
<220> FEATURE:
<221> NAME/KEY: MISC_FEATURE
<222> LOCATION: (1)..(112)
<223> OTHER INFORMATION: Deglycosylated Humanized Antibody Heavy Chain
      Variable Region
<220> FEATURE:
<221> NAME/KEY: MISC_FEATURE
<222> LOCATION: (56)..(56)
<223> OTHER INFORMATION: Xaa at position 56 is any amino acid, provided
      that if Xaa at position 57 is neither Asp nor Pro and Xaa at
      position 58 is Ser or Thr, then Xaa at position 56 is not Asn
<220> FEATURE:
<221> NAME/KEY: MISC_FEATURE
<222> LOCATION: (57)..(57)
<223> OTHER INFORMATION: Xaa at position 57 is any amino acid, provided
      that if Xaa at position 56 is Asn and Xaa at position 58 is Ser or
      Thr, then Xaa at position 57 is Asp or Pro
<220> FEATURE:
<221> NAME/KEY: MISC_FEATURE
<222> LOCATION: (58)..(58)
<223> OTHER INFORMATION: Xaa at position 58 is any amino acid, provided
      that if Xaa at position 56 is Asn and Xaa at position 57 is
      neither Asp nor Pro, then Xaa at position 58 is neither Ser nor
      Thr

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30
```

```
Ser Met Ser Trp Val Arg Gln Ala Pro Gly Lys Gly Leu Glu Leu Val
            35                  40                  45

Ala Gln Ile Asn Ser Val Gly Xaa Xaa Xaa Tyr Tyr Pro Asp Thr Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Ser Gly Asp Tyr Trp Gly Gln Gly Thr Leu Val Thr Val Ser Ser
            100                 105                 110
```

<210> SEQ ID NO 16
<211> LENGTH: 442
<212> TYPE: PRT
<213> ORGANISM: artificial sequence
<220> FEATURE:
<223> OTHER INFORMATION: Humanized antibody
<220> FEATURE:
<221> NAME/KEY: MISC_FEATURE
<222> LOCATION: (1)..(442)
<223> OTHER INFORMATION: Humanized Antibody Heavy Chain
<220> FEATURE:
<221> NAME/KEY: MISC_FEATURE
<222> LOCATION: (56)..(56)
<223> OTHER INFORMATION: Xaa at position 56 is any amino acid, provided
      that Xaa at position 57 is neither Asp nor Pro and Xaa at position
      58 is Ser or Thr, then Xaa at position 56 is not Asn
<220> FEATURE:
<221> NAME/KEY: MISC_FEATURE
<222> LOCATION: (57)..(57)
<223> OTHER INFORMATION: Xaa at position 57 is any amino acid, provided
      that Xaa at position 56 is Asn and Xaa at position 58 is Ser or
      Thr, then Xaa at position 57 is Asp or Pro
<220> FEATURE:
<221> NAME/KEY: MISC_FEATURE
<222> LOCATION: (58)..(58)
<223> OTHER INFORMATION: Xaa at position 58 is any amino acid, provided
      that Xaa at position 56 is Asn and Xaa at position 57 is neither
      Asp nor Pro, then Xaa at position 58 is neither Ser nor Thr

<400> SEQUENCE: 16

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Glu Leu Val
            35                  40                  45

Ala Gln Ile Asn Ser Val Gly Xaa Xaa Xaa Tyr Tyr Pro Asp Thr Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Ser Gly Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
            165                 170                 175
```

```
Leu Ser Ser Val Val Thr Val Pro Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
                260                 265                 270

Tyr Val Asp Gly Val Glu Val His Asn Ala Lys Thr Lys Pro Arg Glu
                275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
                340                 345                 350

Leu Thr Lys Asn Gln Val Ser Leu Thr Cys Leu Val Lys Gly Phe Tyr
                355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430

Gln Lys Ser Leu Ser Leu Ser Pro Gly Lys
                435                 440

<210> SEQ ID NO 17
<211> LENGTH: 16
<212> TYPE: PRT
<213> ORGANISM: Mus sp.
<220> FEATURE:
<221> NAME/KEY: MISC_FEATURE
<222> LOCATION: (1)..(16)
<223> OTHER INFORMATION: Light chain CDR1
<220> FEATURE:
<221> NAME/KEY: MISC_FEATURE
<222> LOCATION: (1)..(16)
<223> OTHER INFORMATION: Light Chain CDR1

<400> SEQUENCE: 17

Arg Ser Ser Gln Ser Leu Val Tyr Ser Asp Gly Asn Ala Tyr Leu His
1               5                   10                  15

<210> SEQ ID NO 18
<211> LENGTH: 17
<212> TYPE: PRT
<213> ORGANISM: Mus sp.
<220> FEATURE:
<221> NAME/KEY: MISC_FEATURE
<222> LOCATION: (1)..(17)
<223> OTHER INFORMATION: Heavy chain CDR2
```

```
<400> SEQUENCE: 18

Gln Ile Asn Ser Val Gly Asn Ser Thr Tyr Tyr Pro Asp Ser Val Lys
1               5                   10                  15

Gly
```